US010977522B2

(12) United States Patent
Anushiravani et al.

(10) Patent No.: US 10,977,522 B2
(45) Date of Patent: Apr. 13, 2021

(54) STIMULI FOR SYMPTOM DETECTION

(71) Applicant: CurieAI, Inc., Santa Clara, CA (US)

(72) Inventors: Ramin Anushiravani, Santa Clara, CA (US); Sridhar Krishna Nemala, Santa Clara, CA (US); Ravi Kiran Yalamanchili, San Jose, CA (US); Navya Swetha Davuluri, Sunnyvale, CA (US)

(73) Assignee: CurieAI, Inc., Santa Clara, CA (US)

( * ) Notice: Subject to any disclaimer, the term of this patent is extended or adjusted under 35 U.S.C. 154(b) by 0 days.

(21) Appl. No.: 16/680,455

(22) Filed: Nov. 11, 2019

(65) Prior Publication Data

US 2020/0152226 A1 May 14, 2020

Related U.S. Application Data

(60) Provisional application No. 62/845,277, filed on May 8, 2019, provisional application No. 62/802,673, filed (Continued)

(51) Int. Cl.
*G06K 9/62* (2006.01)
*G06N 3/04* (2006.01)
(Continued)

(52) U.S. Cl.
CPC .......... *G06K 9/6264* (2013.01); *A61B 5/0205* (2013.01); *A61B 5/0823* (2013.01); (Continued)

(58) Field of Classification Search
CPC ...................................................... G10L 25/66
See application file for complete search history.

(56) References Cited

U.S. PATENT DOCUMENTS 5,715,821 A * 2/1998 Faupel .................... A61B 5/04
600/302
7,207,948 B2 4/2007 Coyle
(Continued)

FOREIGN PATENT DOCUMENTS

CA 2269992 10/2000
JP 2003038460 2/2003
(Continued)

OTHER PUBLICATIONS

Martinez, C. E., and H. L. Rufiner. "Acoustic analysis of speech for detection of laryngeal pathologies." Proceedings of the 22nd Annual International Conference of the IEEE Engineering in Medicine and Biology Society (Cat. No. 00CH37143). vol. 3. IEEE, 2000.*
(Continued)

*Primary Examiner* — Matthew H Baker
(74) *Attorney, Agent, or Firm* — Fish & Richardson P.C.

(57) ABSTRACT

Embodiments are disclosed for health assessment and diagnosis implemented in an artificial intelligence (AI) system. In an embodiment, a method comprises: obtaining, using one or more processors of a device, a speech sample from a user uttering a first sentence; processing the speech sample through a neural network to predict a first set of one or more disease-related symptoms of the user; and generating, using the one or more processors, a second sentence to predict a second set of one or more disease-related symptoms or confirm the first set of disease-related symptoms.

22 Claims, 30 Drawing Sheets

Related U.S. Application Data on Feb. 7, 2019, provisional application No. 62/760,385, filed on Nov. 13, 2018.

(51) Int. Cl.

| | |
|---|---|
| *G16H 10/60* | (2018.01) |
| *G16H 80/00* | (2018.01) |
| *G16H 40/67* | (2018.01) |
| *G16H 50/20* | (2018.01) |
| *A61B 5/08* | (2006.01) |
| *A61B 5/00* | (2006.01) |
| *G06N 3/08* | (2006.01) |
| *G10L 15/02* | (2006.01) |
| *G10L 15/16* | (2006.01) |
| *G10L 15/22* | (2006.01) |
| *G10L 25/66* | (2013.01) |
| *G16H 50/70* | (2018.01) |
| *G16H 20/10* | (2018.01) |
| *G06F 17/16* | (2006.01) |
| *G06F 17/18* | (2006.01) |
| *G16H 70/60* | (2018.01) |
| *G16H 70/40* | (2018.01) |
| *A61B 5/0205* | (2006.01) |
| *A61B 5/11* | (2006.01) |
| *A61B 5/1455* | (2006.01) |
| *G06N 20/10* | (2019.01) |
| *G06K 9/72* | (2006.01) |
| *G10L 15/18* | (2013.01) |
| *A61B 5/024* | (2006.01) |

(52) U.S. Cl.
CPC ............ *A61B 5/11* (2013.01); *A61B 5/14551* (2013.01); *A61B 5/4803* (2013.01); *A61B 5/4815* (2013.01); *A61B 5/4818* (2013.01); *A61B 5/4842* (2013.01); *A61B 5/4848* (2013.01); *A61B 5/6817* (2013.01); *A61B 5/7257* (2013.01); *A61B 5/7264* (2013.01); *A61B 5/7267* (2013.01); *A61B 5/7275* (2013.01); *G06F 17/16* (2013.01); *G06F 17/18* (2013.01); *G06K 9/629* (2013.01); *G06K 9/6257* (2013.01); *G06K 9/6269* (2013.01); *G06K 9/726* (2013.01); *G06N 3/04* (2013.01); *G06N 3/0445* (2013.01); *G06N 3/08* (2013.01); *G06N 20/10* (2019.01); *G10L 15/02* (2013.01); *G10L 15/16* (2013.01); *G10L 15/1815* (2013.01); *G10L 15/22* (2013.01); *G10L 25/66* (2013.01); *G16H 10/60* (2018.01); *G16H 20/10* (2018.01); *G16H 40/67* (2018.01); *G16H 50/20* (2018.01); *G16H 50/70* (2018.01); *G16H 70/40* (2018.01); *G16H 70/60* (2018.01); *G16H 80/00* (2018.01); *A61B 5/024* (2013.01); *A61B 2562/0204* (2013.01); *G10L 2015/027* (2013.01)

(56) References Cited

U.S. PATENT DOCUMENTS

| | | |
|---|---|---|
| 7,479,115 B2 | 1/2009 | Savic |
| 8,241,223 B2 | 8/2012 | Gavriely et al. |
| 8,655,655 B2 | 2/2014 | Wang et al. |
| 8,758,262 B2 | 6/2014 | Rhee et al. |
| 8,764,674 B2 | 7/2014 | Song et al. |
| 8,777,874 B2 | 7/2014 | Zhang et al. |
| 8,784,311 B2 | 7/2014 | Shrivastav et al. |
| 9,526,458 B2 | 12/2016 | MacAuslan |
| 10,098,569 B2 | 10/2018 | Abeyratne et al. |
| 10,223,934 B2 * | 3/2019 | Paul .................... A61B 5/7264 |
| 10,235,998 B1 * | 3/2019 | Khaleghi ............ G10L 15/1815 |
| 2006/0017560 A1 | 1/2006 | Albert et al. |
| 2008/0287821 A1 * | 11/2008 | Jung .................... G06F 19/3418 600/544 |
| 2008/0312547 A1 | 12/2008 | Wada |
| 2009/0192394 A1 | 7/2009 | Guttag et al. |
| 2011/0087079 A1 | 4/2011 | Aarts |
| 2011/0125044 A1 | 5/2011 | Rhee et al. |
| 2012/0131462 A1 | 5/2012 | Chen |
| 2012/0265024 A1 * | 10/2012 | Shrivastav ............... A61B 5/40 600/300 |
| 2013/0060100 A1 | 3/2013 | Wurm et al. |
| 2013/0060150 A1 | 3/2013 | Song et al. |
| 2013/0090927 A1 * | 4/2013 | Quatieri ............... A61B 5/4803 704/249 |
| 2014/0249378 A1 | 9/2014 | Chan et al. |
| 2014/0316220 A1 | 10/2014 | Sheldon |
| 2014/0336537 A1 | 11/2014 | Patel et al. |
| 2015/0073306 A1 * | 3/2015 | Abeyratne ............ G16H 50/20 600/586 |
| 2015/0106020 A1 | 4/2015 | Chung et al. |
| 2015/0245788 A1 | 9/2015 | Schmidt |
| 2015/0265205 A1 * | 9/2015 | Rosenbek ............ A61B 5/4082 600/586 |
| 2015/0269348 A1 | 9/2015 | Madjd |
| 2016/0063997 A1 | 3/2016 | Nemala et al. |
| 2016/0113618 A1 | 4/2016 | Su et al. |
| 2017/0055851 A1 | 3/2017 | Al-Ali et al. |
| 2017/0119302 A1 * | 5/2017 | Rosenbek ............ A61B 5/4082 |
| 2017/0325779 A1 | 11/2017 | Spina et al. |
| 2018/0061396 A1 | 3/2018 | Srinivasan et al. |
| 2018/0092603 A1 | 4/2018 | Duan et al. |
| 2018/0108440 A1 | 4/2018 | Stevens et al. |
| 2018/0206764 A1 | 7/2018 | Ozawa et al. |
| 2018/0346560 A1 | 12/2018 | Breit et al. |
| 2018/0349560 A1 * | 12/2018 | McCloskey .......... A61B 5/0022 |
| 2019/0005021 A1 | 1/2019 | Miller |
| 2019/0104951 A1 | 4/2019 | Valys |
| 2019/0209022 A1 | 7/2019 | Sobol |
| 2019/0221317 A1 * | 7/2019 | Kempanna ............. G16H 50/20 |
| 2019/0304582 A1 | 10/2019 | Blumenthal |
| 2020/0098384 A1 * | 3/2020 | Nematihosseinabadi .................... G10L 15/22 |
| 2020/0152226 A1 * | 5/2020 | Anushiravani ...... G06N 3/0481 |

FOREIGN PATENT DOCUMENTS

| | | |
|---|---|---|
| JP | 2007327993 | 12/2007 |
| JP | 2009233103 | 10/2009 |
| WO | WO 2016142360 | 9/2016 |
| WO | WO 2017167630 | 10/2017 |
| WO | WO 2018107008 | 6/2018 |
| WO | WO 2019005039 | 1/2019 |
| WO | WO 2019122412 | 6/2019 |

OTHER PUBLICATIONS

König, Alexandra, et al. "Automatic speech analysis for the assessment of patients with predementia and Alzheimer's disease." Alzheimer's & Dementia: Diagnosis, Assessment & Disease Monitoring 1.1 (2015): 112-124.*

Karlekar, Sweta, Tong Niu, and Mohit Bansal. "Detecting linguistic characteristics of Alzheimer's dementia by interpreting neural models." arXiv preprint arXiv:1804.06440 (2018).*

Adavanne et al., "A Report on Sound Event Detection with Different Binaural Features," Detection and Classification of Acoustic Scenes and Events, Munich, Germany, Department of Signal Processing, Tampere University of Technology, Nov. 16, 2017, 4 pages.

Amoh et al., "DeepCough: A Deep Convolutional Neural Network in a Wearable Cough Detection System," Thayer School of Engineering, Dartmouth College, Hanover, NH, Sep. 8, 2015, 4 pages.

cc.tut.fi.com [online] "Sound Every Detection in Real Life Audio," available on or before Nov. 2017, via Internet Archive: Wayback Machine URL<https://web.archive.org/web/20171130155008/http://www.cs.tut.fi/sgn/arg/dcase2017/challenge/task-sound-event-detection-

(56) References Cited

OTHER PUBLICATIONS in-real-life-audio-results>, retrieved on Nov. 12, 2019, URL <<http://www.cs.tut.fi/sgn/arg/dcase2017/challenge/tasksound-event-detection-in-real-life-audio-results>, 6 pages.
Chen et al., "Acoustic Source Localization and Beamforming: Theory and Practice," EURASIP Journal on Applied Signal Processing, Mar. 30, 2003, 4:359-370.
Chen et al., "DCASE2017 Sound Event Detection Using Convolutional Neural Networks," Detection and Classification of Acoustic Scenes and Events 2017, Munich, Germany, Department of Electrical and Computer Engineering, University of Rochester, Nov. 16, 2017, 3 pages.
deepnotes.com [online], "Classification and Loss Evaluation—Softmax and Cross Entropy Loss," available on or before Jun. 19, 2017, via Internet Archive: Wayback Machine URL <https://web.archive.org/web/20180307170119/https://deepnotes.io/softmax-crossentropy>, retrieved on Nov. 13, 2019, URL <https://deepnotes.io/softmax-crossentropy>, 14 pages.
Di Perna et al., "An automated and unobtrusive system for cough detection," IEEE Life Sciences Conference, Dec. 13, 2017, pp. 190-193.
Diep, "Classification of Cough Events," Thesis for ECE Senior Capstone Project, Tufts University, Department of Electrical and Computer Engineering, 2017, 4 pages.
Drugman et al., "Audio and Contact Microphones for Cough Detection," TCTS Lab—University of Mons, Belgium, Pediatric Pulmonology & Cystic Fibrosis Unit, Cliniques St Luc, University of Louvain, Belgium, Sep. 2012, 4 pages.
github.com, [online], "Models for AudioSet: A Large Scale Dataset of Audio Events," available on or before May 30, 2018, via Internet Archive: Wayback Machine URL <https://web.archive.org/web/20180530092859/https://github.com/tensorflow/models/tree/master/research/audioset>, retrieved on Nov. 14, 2019, URL<https://github.com/tensorflow/models/tree/master/research/audioset>, 1 page.
Hou et al., Sound Event Detection in Real Life Audio Using Multi-Model System, Detection and Classification of Acoustic Scenes and Events, Munich, Germany, Nov. 16, 2017, 5 pages.
Kadambi, "Towards a Wearable Cough Detector Based on Neural Networks," IEEE International Conference on Acoustics, Speech and Signal Processing, Apr. 15, 2018, pp. 2161-2165.
Larson et al., "Accurate and Privacy Preserving Cough Sensing using a Low-Cost Microphone," UbiComp'11, Paper Session: How Healthy?, Beijing, China, Sep. 17-21, 2011, 375-384.
Larson et al., "Validation of an Automated Cough Detection Algorithm for Tracking Recovery of Pulmonary Tuberculosis Patients," PLoS ONE, Oct. 10, 2012, 7:1-10.
Lee et al., "Sound: a non-invasive measure of cough intensity," BMJ Open Resp Res., May 1, 2017, 4:1-9.
machinelearningmastery.com [online], "A Gentle Introduction to Mini-Batch Gradient Descent and How to Configure Batch Size," available on or before Jul. 24, 2017, via Internet Archive: Wayback Machine URL<https://web.archive.org/web/20170724025756/https://machinelearningmastery.com/gentle-introduction-mini-batch-gradient-descent-configure-batch-size/>, retrieved on Nov. 13, 2019, URL<https://machinelearningmastery.com/gentle-introduction-mini-batch-gradient-descent-configure-batch-size/>, 22 pages.
machinelearningmastery.com [online], "Gentle Introduction to the Adam Optimization Algorithm for Deep Learning," available on or before Aug. 4, 2017, via Internet Archive: Wayback Machine URL <https://web.archive.org/web/20170804104210/https://machinelearningmastery.com/adam-optimization-algorithm-for-deep-learning/>, retrieved on Nov. 13, 2019, URL <https://machinelearningmastery.com/adam-optimization-algorithm-for-deep-learning/>, 13 pages.
Moradshahi et al., "Cough sound discrimination in noisy environments using microphone array," IEEE International Instrumentation and Measurement Technology Conference, Department of Systems and Computer Engineering Carleton, University, Ottawa, Canada May 6-9, 2013, 4 pages.
Rao et al., "Improved Detection of Lung Fluid with standardized Acoustic Simulation of the Chest," IEEE J. Transl. Health Med, Aug. 21, 2018, 6:1-7.
Sterling et al., "Automated Cough Assessment on a Mobile Platform," Journal of Medical Engineering, Aug. 20, 2014, 2014:951621: 1-10.
Vingayls et al., "Show and Tell: A Neural Image Caption Generator," IEEE Conference on Computer Vision and Pattern Recognition, Jun. 7, 2015, pp. 3156-3164.
U.S. Appl. No. 16/680,429, filed Nov. 11, 2019, Anushiravani et al.
U.S. Appl. No. 16/680,437, filed Nov. 11, 2019, Anushiravani et al.
U.S. Appl. No. 16/680,453, filed Nov. 11, 2019, Anushiravani et al.
U.S. Appl. No. 16/680,458, filed Nov. 11, 2019, Anushiravani et al.
Deshpande [online], "The 9 Deep Learning Papers You Need to Know About (Understanding CNNs Part 3)," Engineering at Forward : UCLA CS '19, Aug. 24, 2016, retrieved on Apr. 23, 2020, retrieved from URL <https://adeshpande3.github.io/adeshpande3.github.io/The-9-Deep-Learning-Papers-You-Need-To-Know-About.html>, 20 pages.
Deshpande [online], "Deep Learning Research Review Week 3: Natural Language Processing," Engineering at Forward: UCLA CS '19, Jan. 10, 2017, retrieved on Apr. 23, 2020, retrieved from URL <https://adeshpande3.github.io/Deep-Learning-Research-Review-Week-3-Natural-Language-Processing>, 20 pages.
Deshpande [online], "A Beginner's Guide to Understanding Convolutional Neural Networks," Engineering at Forward : UCLA CS, Jul. 20, 2016, retrieved on Apr. 23, 2020, retrieved from URL <https://adeshpande3.github.io/A-Beginner%27s-Guide-To-Understanding-Convolutional-Neural-Networks/>, 16 pages.
Deshpande [online], "A Beginner's Guide to Understanding Convolutional Neural Networks Part 2," Engineering at Forward : UCLA CS '19, Jul. 29, 2016, retrieved on Apr. 23, 2020, retrieved from URL <https://adeshpande3.github.io/adeshpande3.github.io/A-Beginner's-Guide-To-Understanding-Convolutional-Neural-Networks-Part-2/>, 7 pages.
Minar et al., "Recent Advances in Deep Learning: An Overview," Cornell University Library, Jul. 18, 2018, pp. 1-31.
PCT Invitation to Pay Additional Fees in International Appln. PCT/US2019/060968, dated Apr. 22, 2020, 18 pages.
Sun et al., "SymDetector: Detecting Sound-Related Respiratory Symptoms Using Smartphones," UBICOMP, Osaka, Japan, Sep. 7-11, 2015, 97-108.
Uwaoma et al., "Towards real-time monitoring and detective monitoring of asthma symptoms on resource-constraint mobile device," IEEE Consumer Communications and Networking Conference, Jan. 2015, pp. 47-52.
Vuppalapati et al., "Artificial Intelligence (AI) Infused Cow Necklace—for Diagnosis of Bovine Respiratory Diseases," 2018 International Conference on Machine Learning and Cybernetics, Chengdu, China, Jul. 15-18, 2018, 222-229.
PCT International Search Report and Written Opinion in International Appln. PCT/US2019/060968, dated Jun. 24, 2020, 24 pages.
International Preliminary Report Written Opinion in International Appln. No. PCT/US2019/060968, dated Oct. 8, 2020, 13 pages.
U.S. Appl. No. 17/001,522, filed Aug. 24, 2020, First Named Inventor Anushiravani et al.

* cited by examiner

STIMULI FOR SYMPTOM DETECTION

CROSS-RELATED APPLICATIONS

The application claims the benefit of priority from U.S. Provisional Patent Application No. 62/760,385, filed Nov. 13, 2018, for "Intelligent Health Monitoring," and U.S. Provisional Patent Application No. 62/802,673, filed Feb. 7, 2019, for "Intelligent Health Monitoring," and U.S. Provisional Patent Application No. 62/845,277, filed May 8, 2019, for "Always-On Passive Health Monitoring," which provisional patent applications are each incorporated by reference herein in its entirety.

TECHNICAL FIELD

The disclosed subject matter relates generally to health monitoring, and more particularly to health monitoring using multimodal sensors and other external data captured manually.

BACKGROUND

Health assessment and diagnosis of specific disease conditions is performed based on data from measurements of a relevant set of biomarkers. A health assessment can also include determining the disease state, severity and progression. Vital signs like pulse rate, temperature, respiration rate and blood pressure are measured using a variety of sensors. These measurements are taken one time or continuously/intermittently over an extended period of time. For example, while a fever diagnosis can simply be done based on a single temperature measurement, a diagnosis of hypertension requires at least three blood pressure readings taken at least one week apart. A diagnosis of obstructive sleep apnea requires continuous measurement of heart, lung and brain activity, breathing patterns, arm and leg movements, and blood oxygen levels while the patient is asleep for at least 4 hours.

SUMMARY

In this disclosure, a number of embodiments are disclosed for health assessment and diagnosis implemented in an artificial intelligence (AI) system. The AI system takes as input information from a multitude of sensors measuring different biomarkers in a continuous or intermittent fashion. The proposed techniques disclosed herein address the unique challenges encountered in implementing such an AI system.

More particularly, health monitoring techniques are disclosed herein that monitor disease conditions and vital signs of one or more users for a short or long period of time continuously or when prompted. The disclosed embodiments include systems, methods, apparatuses and computer program products for collecting sensory information using one or more sensors, such as one or more microphones, a digital stethoscope, a peak flow meter, a pulse oximeter, peripheral capillary oxygen saturation (SPO2) sensor, radio frequency (RF) transceivers, and a portable ultrasound, Polysomnography sensors (PSG), etc. In addition to sensory information, other user information is collected, including but not limited to: age, gender, abnormal vital signs, prescribed and over-the-counter medications, geolocation, daily activities, diet, and any other information that can be used to predict (e.g., using proprietary machine learning and advanced statistical signal processing algorithms) the user's symptoms. The user's symptoms may include but are not limited to: coughing, snoring, teeth grinding, wheezing, etc.

In addition to predicting the user's symptoms, the system predicts the user's disease or disease state, if any, as well as possible future disease states, identifies triggers, determines whether a particular medication prescribed to the user is effective in managing the symptoms and/or disease or disease state and determines multiple conditions other than respiratory conditions, such as sleep disorders, sleep stages (e.g., REM stages and Deep sleep) using the collected sensory and user information.

In an embodiment, a method comprises: obtaining, using one or more processors of a device, a speech sample from a user uttering a first sentence; processing the speech sample through a neural network to predict a first set of one or more disease-related symptoms of the user; and generating, using the one or more processors, a second sentence to predict a second set of one or more disease-related symptoms or confirm the first set of disease-related symptoms.

Other embodiments are directed to systems, apparatuses and non-transitory, computer-readable mediums.

For simplicity, only a few symptoms are discussed in the description that follows. It should be noted, however, that the disclosed embodiments can monitor any number of symptoms, vital signs, and collect any suitable data to use in predicting the user's symptoms, disease or disease state based on the symptoms, and/or whether a particular medication prescribed to the user is effective in managing the symptoms and/or disease or disease state, etc.

Embodiments disclosed herein can be applied to fall detection as falling down is common in elderly people. For example, a fall is often followed by moaning sounds from the pain that can be captured by the system and used to alert an authority or a relative. The disclosed embodiments can also be used in pharmaceutical clinical trials to get a more consistent and accurate assessment of the medication effectiveness on a controlled patient group quickly and cost effectively.

DETAILED DESCRIPTION OF EXAMPLE EMBODIMENTS

Figure 1A:
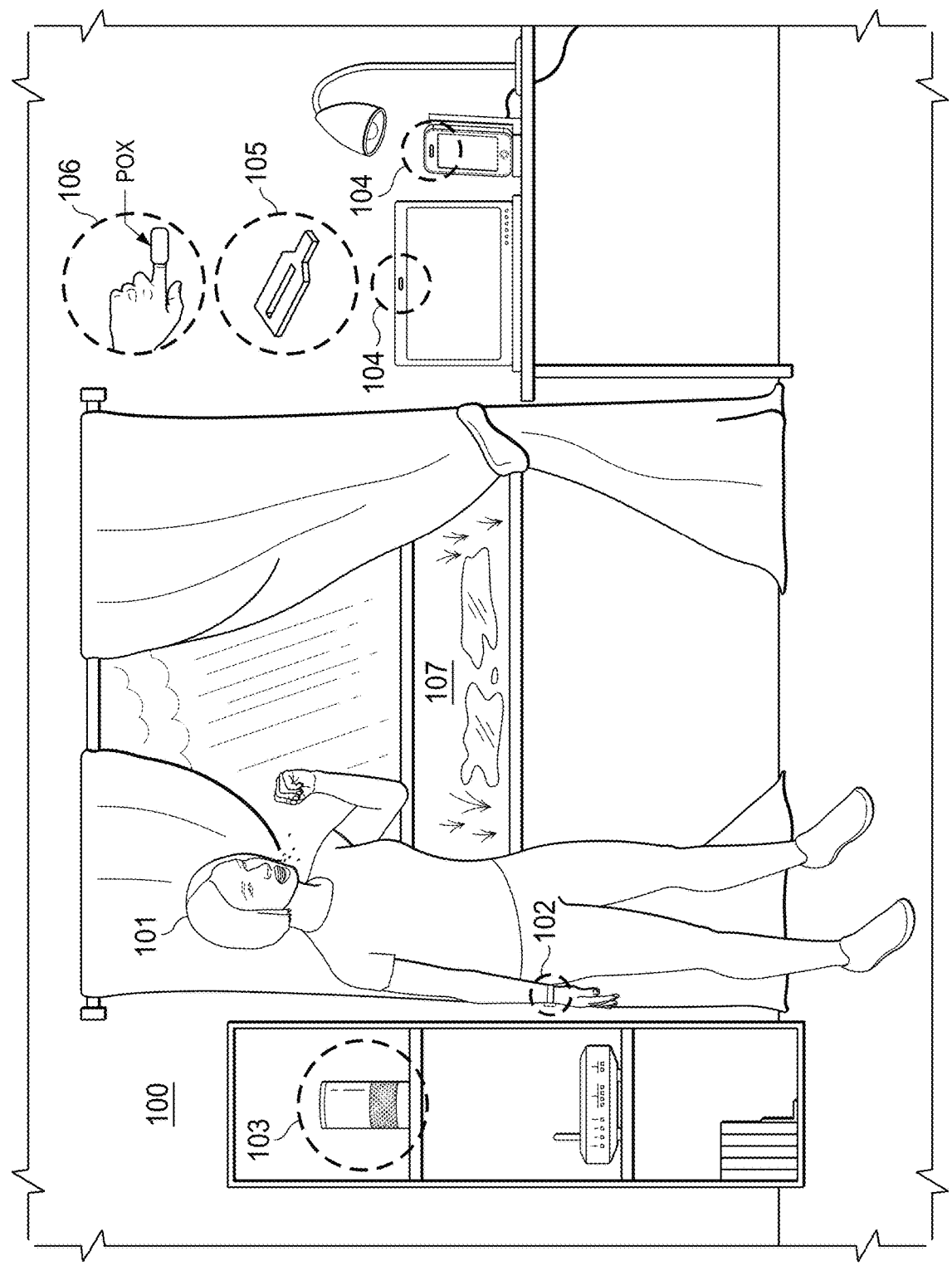
FIG. 1A illustrates how sensory data from different sensors are captured, according to an embodiment.

FIG. 1A illustrates how sensory data from different sensors are captured, according to an embodiment. User 101 is shown coughing in environment 100 (e.g., the patient's home). Various sensors are included in the environment 100 that capture the cough. For example, a first sensor 102 is a smartwatch which is worn on the wrist of user 101 and includes one or more microphones and an audio subsystem for capturing ambient sound in environment 100. A second sensor is notebook computer 103 that includes one or more microphones and audio subsystem for capturing the ambient sound in the environment 100. A third sensor is a smart speaker 103 that includes one or more microphones and an audio subsystem for capturing the ambient sound in the environment. In this example, all three sensors 102, 103, 104 have each captured audio of the coughing and stored the audio in a local file system. The audio is then processed as described in this disclosure and/or is transmitted to another device or network for further analysis using some, or all the techniques described herein.

In addition to sensors 102, 103, 104, fourth sensor 105 is an electronic thermometer for determining the body temperature of the user 101, and a fifth sensor 106 is blood pressure monitor for determining the blood pressure of the user 101. The sensors 102, 103, 104, 105 and 106 are examples of possible sensors that can be used with the disclosed AI system. Other sensors can also be used by the AI system, including but not limited to: a digital stethoscope, a peak flow meter, a pulse oximeter, radio frequency transceivers, a portable ultrasound and any other sensor capable of measuring or capturing information related to the physical or mental health of the user 101.

Figure 1B:
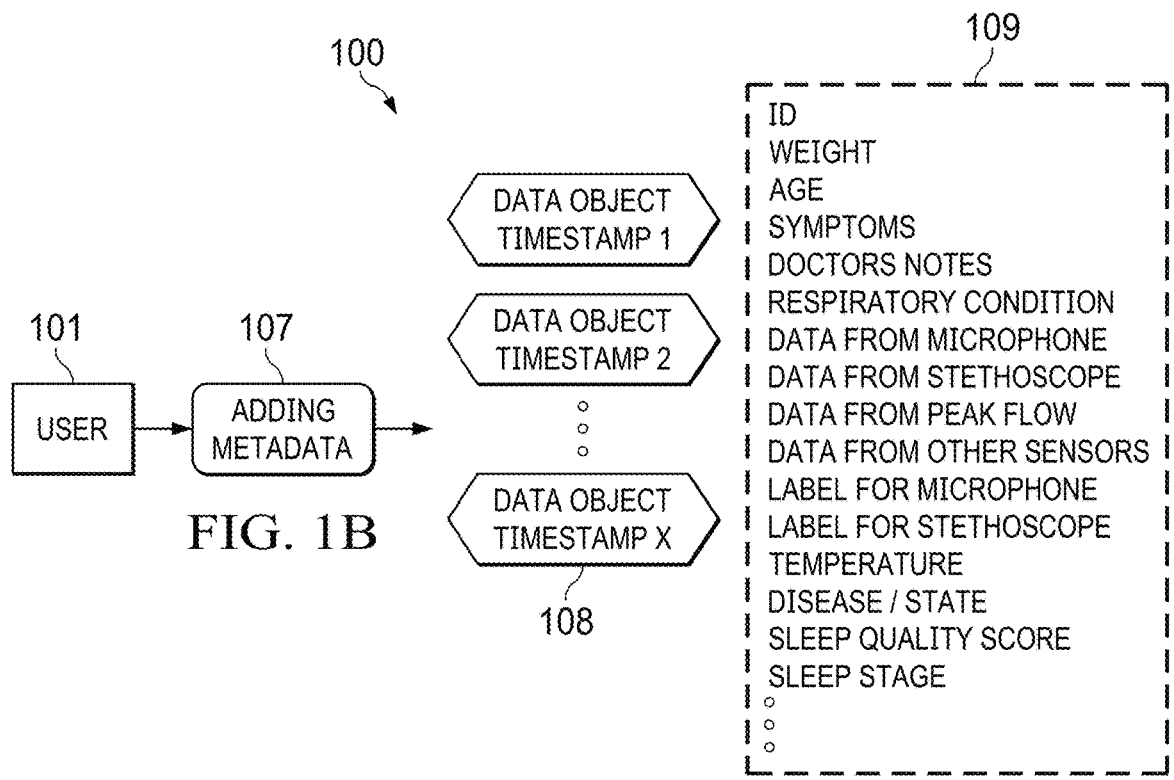
FIG. 1B is a graphical illustration of adding metadata to collected data from each user, according to an embodiment.

FIG. 1B is a graphical illustration of how data from different sensors are annotated for each user, according to an embodiment. For example, a user 101 can be represented by one data object 108 per monitoring session. The user data object 108 can include sensory data and other user data that can be added as metadata 107 to the user data object 108. Examples of data 109 stored in the user data object 108, include but are not limited to: the user's vital information (vital signs) at the time of monitoring, the user's symptoms, and sensory data collected from the user during the monitoring. The sensory data can include but is not limited to: data collected from a microphone or a number of microphones, digital stethoscope, peak flow meter or any other suitable sensors. Note that not all user data referenced above will be available for each data object at each timestamp. Some of the user data may be discovered later through one or more of the embodiments described herein. In an embodiment, the user data object is encrypted to protect user privacy. In addition to sensory data, the data 109 may include but are not limited to: user ID, weight, age, symptoms, doctors notes, know respiratory condition, sleep quality score, sleep stages, and sleep disorders, etc.

In an embodiment, the monitoring is performed by a health monitoring device, including but not limited to: a smartphone, smart speaker, tablet computer, desktop computer, notebook computer, wearable computer (e.g., smart watch, fitness band) and any other suitable electronic device. The sensors (e.g., microphones) can be embedded in or coupled to an I/O port of the health monitoring device as an accessory.

The health monitoring device can include one or more processors, memory (e.g., flash memory) for storing instructions and data, power source (e.g., a battery), wireless connectivity (e.g., a wireless transceiver) for wirelessly communicating with a network (e.g., the Internet, local area network) access point (e.g., WiFi router, cell tower) or directly with another device (e.g., Bluetooth, Near Field Communications, RFID), a display (e.g., a display) and/or other output devices (e.g., loudspeaker), input device(s) (e.g., touch sensitive display, mechanical buttons, dials, etc.) and one or more I/O ports (e.g., USB, Thunderbolt, Ethernet, etc.) for coupling to accessory devices. In an embodiment, one or more of the methods/processes/features described below is at least partially implemented/performed on a second device, such as a network server computer, companion device, medical instrument or machine that is wirelessly coupled (or wired) to the health monitoring device.

Figure 2:
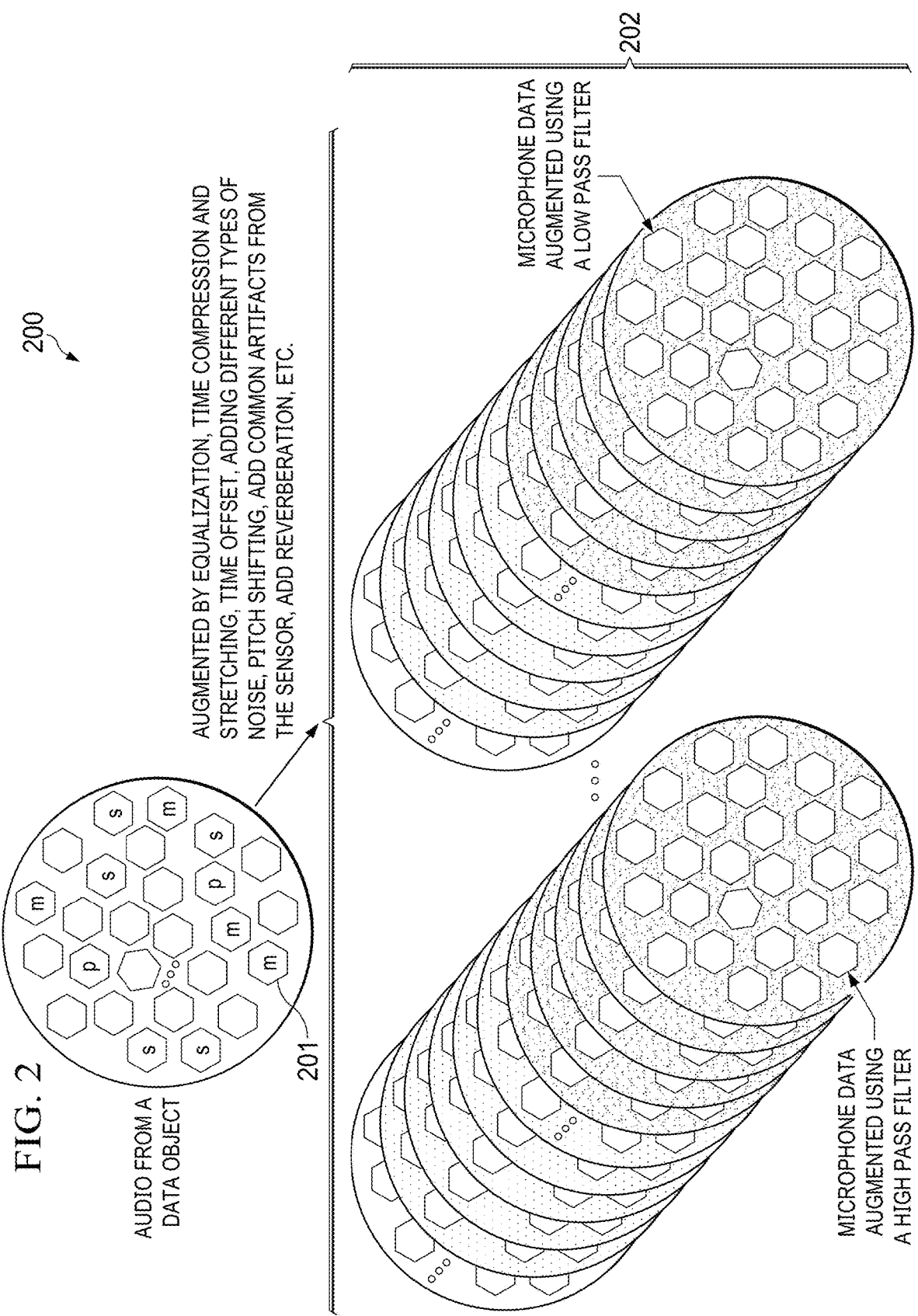
FIG. 2 illustrates a system for modelling and applying variabilities for collected audio data for each data object, according to an embodiment.

FIG. 2 is a block diagram for modelling acoustical and post-processing variability for collected audio data for each data object, according to an embodiment. The augmentation system depicted in FIG. 2 models variability in audio signals captured by acoustical sensors and augments the data objects to create realistic example data objects. The data objects are then used to train one or more learning algorithms in accordance with the example embodiments disclosed herein.

In a first step, audio data 201 from a data object 108 is collected. If the data is collected by a microphone (denoted as "m"), the data is augmented using an equalization technique. The equalization technique randomly manipulates the frequency response of the audio data using one or more of a low pass, band pass, high pass or stop band filter to simulate different microphone frequency responses, device placement, and different acoustical environments. In another embodiment, if the data is collected by a digital stethoscope (denoted as "s") then a different set of equalization filters is used to augment the audio data (e.g., with a focus on capturing device placement variability). Each audio data may also be modified using one or more of the following audio processes: time stretching, time compressing, shifting in time, pitch shifting, adding background noise at different ratios, adding or removing reverberation, etc. The augmentation described above creates many different variations for each data object 108, wherein each variation includes audio data that has been augmented differently than the original recorded audio data and the other audio objects.

Since different sensors have different sampling rates and usage they need to be pre-processed differently before their output is fused and enters the feature extraction stage described below. For example, a microphone sampling rate is usually from 200 Hz to 20000 Hz and a microphone that is operating continuously captures symptoms for every timestamp.

A digital stethoscope, however, usually has a sampling rate between 50 Hz to 2000 Hz. Because a digital stethoscope needs to be placed on a user's chest, lungs or back, there may be more than one spot that needs to be recorded. Such recordings are usually done once or twice a day.

Another use case for a digital stethoscope is described in Adam Rao et al., "Improved Detection of Lung Fluid with Standardized Acoustic Simulation of the Chest," IEEE J. Transl. Eng. Health Med. 2018; 6: 3200107. In this paper, the authors discuss a technique where a low frequency chirp signal is sent through the patient's chest and recorded through a digital stethoscope on the patient's back. The recorded chirp signal can then be analyzed to find any abnormalities and infections in the lungs that can be a sign for a respiratory disease and possible sleep disorders. More discussions on how data from multiple sensors are fused follows in later sections of this disclosure.

A peak flow meter might be used once or twice a day. The most common peak flow meters are analog. They usually display a number representing the air flow and the degree of obstruction in the user's airways. This metric can be entered manually by the user through an application and later be added as another feature that can be used by the system to make better and further inference. Again, such a metric is not present for most of the day and is captured when a user is prompted to use a peak flow meter, say every night at 8:00 PM.

A pulse oximeter is usually available digitally and measures a user's oxygen saturation level. For simplicity and the user's comfort, the user might be prompted to measure their oxygen saturation level only once or twice a day or when needed. Recent developments in pulse oximeter technology suggest that continuous pulse oxygen could be made available through smart watches to infer a patient's state more accurately and with higher resolution.

Fusing different sensors is not a trivial task. Some sensors are used more frequently than others and each sensor could represent one or more numbers that could be on a completely different scale. The details of a fusing mechanism used in the disclosed AI system are discussed in reference to FIG. 4. Based on the type of sensors used and their availability at a current time-stamp, the sensors are synced in a predetermined time-resolution. A feature vector is created using the sensor data. The feature vector can be sparse at a certain time-stamp depending on data availability. The feature vector is fed to an algorithm for inference.

Figure 3C:
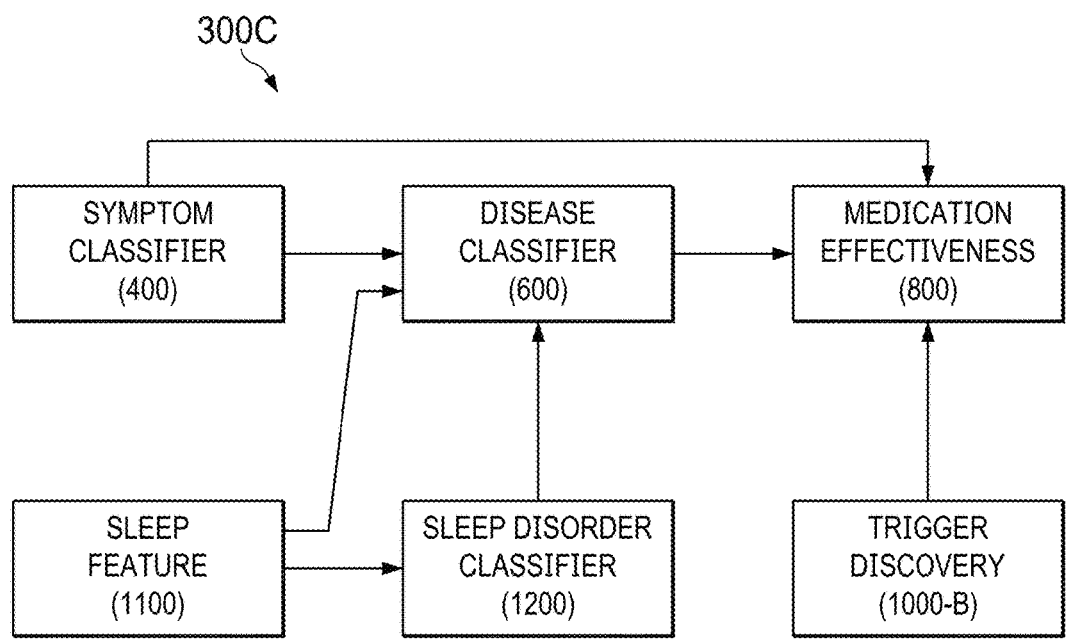
FIG. 3C is a graphical illustration of the overall architecture of the classifiers used in the intelligent health monitoring system, according to an embodiment.
Figure 3A:
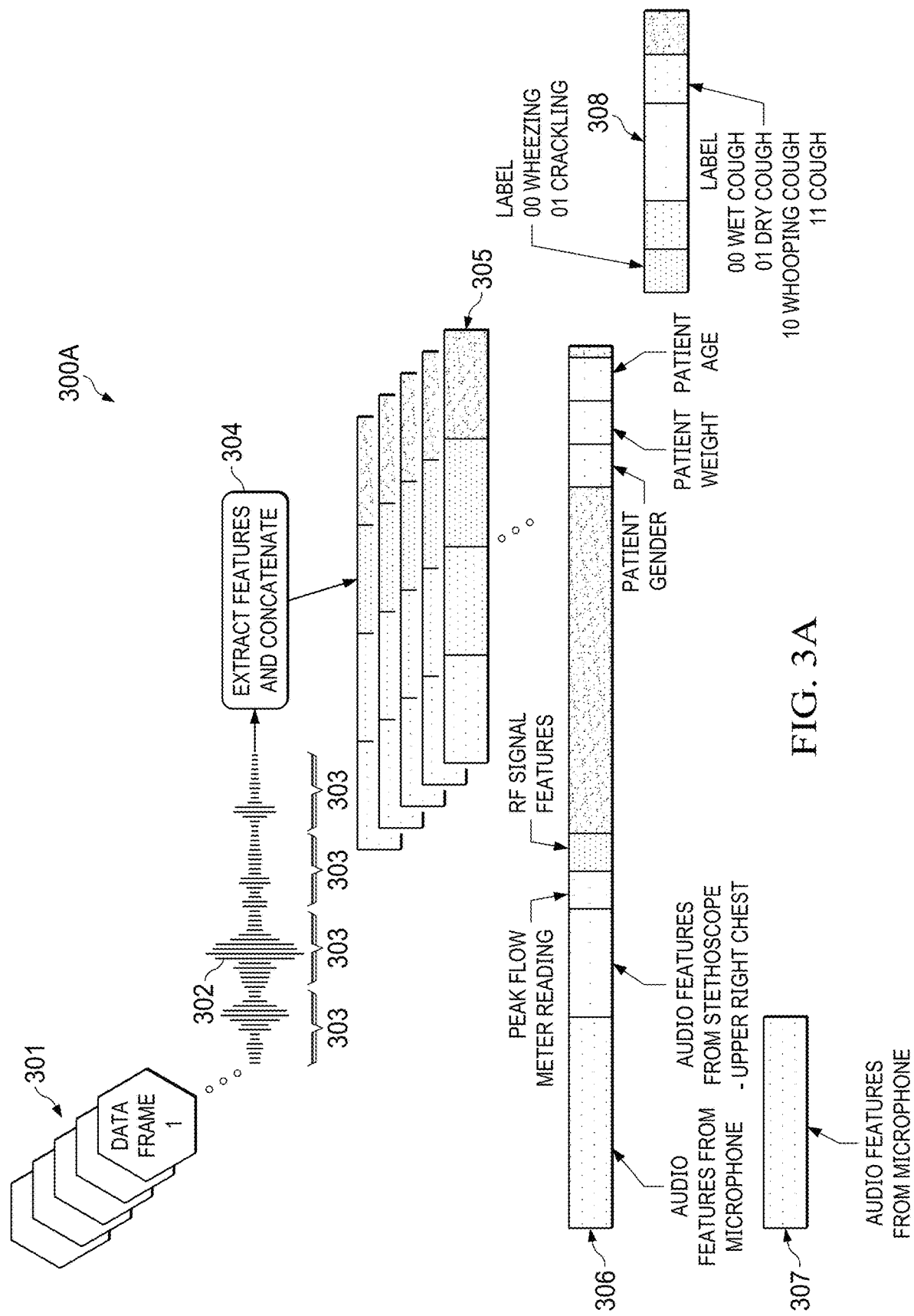
FIG. 3A is a schematic diagram of feature extraction from the auditory data from each data object, according to an embodiment.

FIG. 3A is a schematic diagram of feature extraction from the auditory data from each user data object, as well as feature concatenation from other sensory data, according to an embodiment. The feature extraction method shown at the top of FIG. 3A extracts low dimensional features from time-domain audio signals captured by one or more microphones and a digital stethoscope or other auditory data. The details of the feature extraction could be different based on the sensor specification. These features are generally much lower in dimensionality and attempts to capture signatures from different audible symptoms. These features are later used in a process to guide a learning network in understanding symptoms from all user data objects.

In an embodiment, each audio signal is analyzed frame by frame (e.g., a consecutive group of audio samples) (301). Each frame of the data can be anywhere between 64 milliseconds to 512 milliseconds in length to capture the audio characteristics of one event. Each frame can then be divided into four or more equally spaced sub-frames based on the frame size (302, 303). Such features can include but are not limited to: Mel Frequency Cepstral Coefficients (MFCC), Discrete Cosine Transform coefficients (DCT), Fast Fourier Transform (FFT) coefficients, zero crossing rate, dynamic range, spectral flatness and spectral flux. In some embodiments, features are extracted from the whole frame and concatenated with the subframe feature vector. Feature extraction is then performed on each subframe and the resulting features are concatenated together (304, 305) into a combined feature vector along with features from other sensory data and other available resources, such as the pollen count at that time-stamp from the user's location.

Once features are extracted from the user data objects they are used to train a neural network that detects particular symptoms. For example, audio features at a certain time-stamp that correspond to a cough sound, along with other current information obtained from the user data object (e.g., weight and gender of the patient), are used in the feature vector 305. In an embodiment, some of the information is hot encoded, so that the information can be mathematically represented in the feature vector (306). For example, the gender of the patient if female can be hot coded as "0" and if the gender is male, it can be hot coded as "1" at a predetermined position in the feature vector.

As mentioned earlier, some of these data might be missing. In such cases, an equalizer drop-out is applied to the input layer of the neural network so that the neural network learns to focus on the available information. A label vector is also created (308) that tracks the labels corresponding to a feature vector. The label vector is used later when training parallel, cascaded, and multitask classifiers that learn how to map features to their corresponding labels.

Two other methods were also developed for extracting more interesting features from the auditory data in each data object.

Figure 3B:
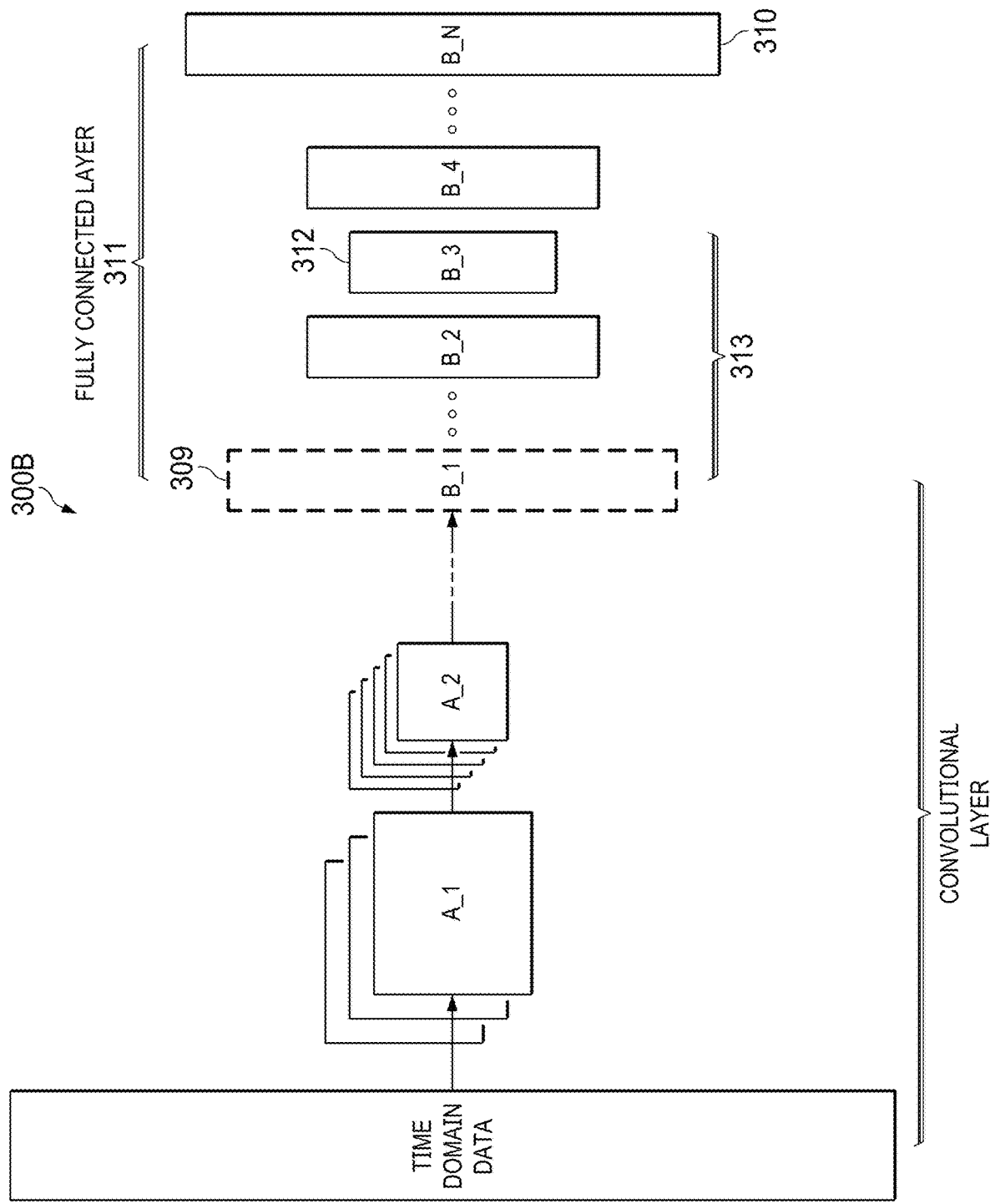
FIG. 3B illustrates a process of extracting features from raw data captured from the sensors using a neural network, according to an embodiment.

FIG. 3B illustrates extracting features from raw data from the sensors using a bottle-neck convolutional neural network (CNN), according to an embodiment. More particularly, a method is illustrated for deriving features from auditory data as opposed to manually designed features discussed earlier. In the first example shown, the time domain audio signal is passed to a neural network. During training, the output layer of the CNN (309) represents the concatenation of different auditory features, such as dynamic range and zero crossing of the data. During testing, the weights and biases from the training are fixed and the time domain data is propagated forward through the network, wherein the output layer represents the newly learned feature vector (309).

Training a deep CNN may be computationally time consuming and demanding. As such another method for extracting meaningful features could start at (309), wherein the output feature vector has already been determined by transforming the time domain signal to a more well-known time-frequency representation, such as short-time Fourier Transform (STFT), Fast Fourier Transform (FFT), Discrete Cosine Transform (DCT), or modified DCT (MDCT).

Once a feature-like vector in the output layer of CNN is provided (309), it is passed through a pre-trained feedforward neural network to determine a final feature vector (312). During training of this feedforward neural network (309 to 310), the output layer (310) represents manually hand-designed features, such as Mel-frequency Cepstral Coefficients (MFCC), FFT, Zero Crossing Rate, Spectral Flatness, a one-hot encoded label corresponding to the data, etc. Using backward propagation, the neural network learns weights and biases that propagate the input spectrum like feature to the manually designed feature automatically. Once weights and biases are determined, the middle layer of this feedforward neural network (312) represents the final features that are extracted by the neural network, and used to train the model. When performing inference, only layers up to B_3 (312, highlighted by 313) are used to extract the final features. Such neural networks are also known as "autoencoders," wherein an audio signal is first encoded to a lower dimensional feature space (312) and then the encoded feature vector (312) is decoded to a desired higher dimensional feature space. The feature extraction scheme described above can replace the feature extraction described in reference to FIG. 3-A.

Another advantage of the feature extraction scheme described above is that the neural network can learn to clean features so that the extracted features are uncorrelated between all classes, allowing the model to perform more accurately. For example, features from a noisy data (which can be achieved synthetically, 204) are the input to the network and the labels, i.e., ground truth, are the corresponding clean data features. Such a network learns to denoise the data as part of the feature extraction, thus creating features that are more robust to noise (310).

If there is more than one microphone available, a weighted average of the microphone signals (e.g., output from a MVDR beamformer) is fed to the feature extraction network. In many cases, a digital stethoscope is usually placed at upper, lower, left and right areas of the chest and back, adding up to 8 different locations and signals. These signals are fed to the feature extraction network, which results in 8 feature vectors. The peak flow meter and pulse oximeter each output one number which is directly placed in the feature vector when available.

FIG. 3C is a graphical illustration of an example architecture for the classifiers described in this disclosure, according to an embodiment. In particular, FIG. 300C depicts a general relationship between some of the classifiers discussed in this disclosure. A symptom classifier output is fed to a diseases classifier. A disease classifier uses a sleep feature vector and predicted sleep disorder (discussed later) to predict a patient's disease or disease state. A medication effectiveness classifier measures the effectiveness of a prescription using the predicted disease or disease state and discovered triggers.

Figure 4:
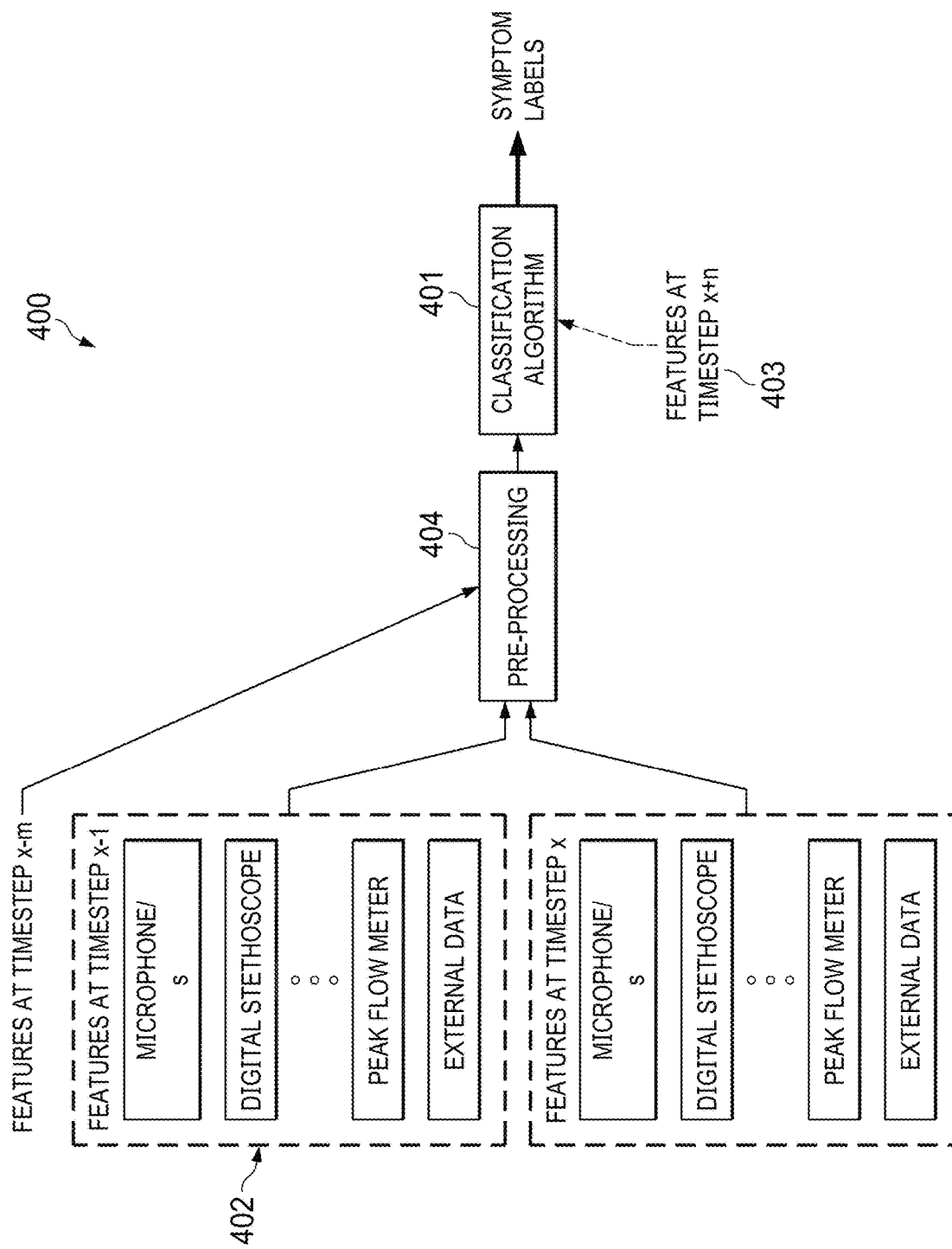
FIG. 4 is a graphical illustration of a classification process, wherein the feature vector at each timestamp is fed to the model and outputs a probability for pre-determined symptoms, according to an embodiment.

FIG. 4 is a graphical illustration of a classification process wherein features extracted from the raw data from each sensor are concatenated at each timestamp along with other features, according to an embodiment. In particular, FIG. 4 depicts a classification algorithm wherein a number of features are extracted from available sensory signals (300A, 300B) and other available features (307) and then used as input to the classification model as mentioned earlier. These feature vectors are then feed to a classification algorithm (401) that predicts user's symptoms (e.g., coughing, wheezing, type of the cough if any, snoring, teeth grinding, shortness of breath, agonal breathing, etc.) for the user at each timestamp. In an embodiment, such a network is first trained offline using ground truth labels and its corresponding data, and then the parameters of the model are fixed during inference.

In another example embodiment where the data has been collected for a fixed period of time, the features from future timestamps (403) are used in addition to the current and past timestamp features. Such features are collectively feed to a preprocessing step (404). In the preprocessing step, the data is normalized using the mean and standard deviation of the training dataset. As discussed earlier, since each sensor has its own sampling rate that has a different frequency, there may be missing features for most of the timestamps. In such cases, missing data can be replaced by predetermined or past values.

Figure 5:
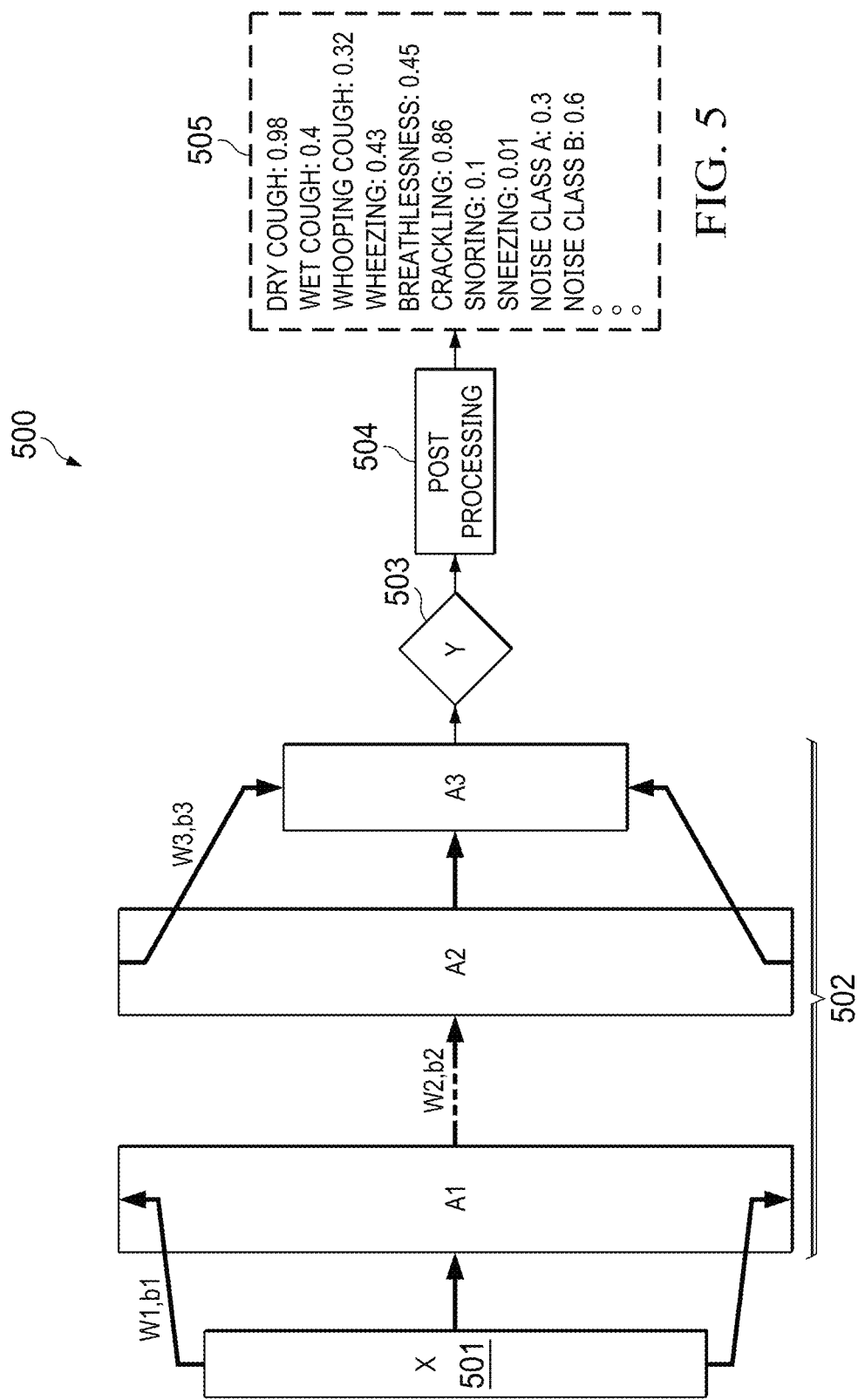
FIG. 5 is a graphical illustration of a respiratory event classification algorithm using a neural network, according to an embodiment.

FIG. 5 is a graphical illustration of a multitask symptom classification algorithm using a deep neural network, according to embodiment. The classification system described in 401 is depicted in FIG. 5 as a neural network with three hidden layers. The depicted number of hidden layers and the size of each layer should only be considered as examples to better understand the embodiments described herein, and are not intended to limit the scope of the claimed subject matter. The neural network shown in FIG. 5 can have 2 or more hidden layers and the number of units for each hidden layer can vary based on the data presented from each sensor and available external information. These hyperparameters are subject to change based on the hardware, data, and desired recall and precision.

In an embodiment, the feature vector (501) is fed to a pre-trained feedforward neural network. The number of units in the output layer equals the number of conditions (503). The posterior vectors (503) are then fed to a post processing method that predicts the most likely symptoms (505).

The mathematical equation for the neural network shown in FIG. 5 is depicted in Equation 1.

$$Y = \theta_3((W_3 * (\theta_2(W_2 * (\theta_1(W_1 * X + b_1)) + b_2)) + b_3) \quad [1]$$

wherein X is the feature vector (501), Y is the output layer containing the posterior probabilities of each possible condition occurring, $W_i$ and $b_i$ are weights and biases corresponding to each layer, and $\theta_1$ and $\theta_2$ are the relu nonlinearity functions applied to each unit in the first and second hidden layers. A relu function is defined in Equation [2]:

$$y = \max(x, 0), \quad [2]$$

wherein y is the output of the relu function and x is the input function.

$\theta_3$ is a softmax function applied to the last hidden layer as defined in Equation [3]:

$$F(x_i) = \frac{\exp(x_i)}{\sum_{j=0}^{k} \exp(x_i)}, \quad [3]$$

wherein $x_i$ is the input vector to a softmax function.

In an embodiment, the classification system (500, 401) is trained offline using the originally labeled dataset and the augmented dataset (204). Regularization is applied to each layer to avoid overfitting the model to training dataset as well as making the model robust to missing data. To lower the computational intensity the features are quantized and fed to the network in mini batches as opposed to the whole batch at once. An example of this method is described in (https://machinelearningmastery.com/gentle-introduction-mini-batch-gradient-descent-configure-batch-size/). A cross entropy loss function, such as the example method described in (https://deepnotes.io/softmax-crossentropy) between the output units (503) and the true labels is then used. Such cost functions are then minimized using optimizers, such as an Adam Optimizer, as described in (https://machinelearning-mastery.com/adam-optimization-algorithm-for-deep-learning/). A cross entropy loss function is defined in Equation 4.

$$\text{loss} = -\Sigma_{j=1}^{M} \log(P_{i,j}) \quad [4]$$

wherein $p_{i,j}$ refers to the probability of an observation i given class j (i.e., the posterior vector) and y is a binary vector of 0s or 1s wherein if a class j is the correct classification for observation i then y is set to 1 and 0 otherwise.

The weights and bias coefficients learned from such processes are then fixed in the classification system, the feedforward neural network, (500, 401), to predict symptoms for each timestamp.

As described above, a feedforward neural network was trained in a supervised fashion using the data collected earlier (104) to assign various labels to different combinations of features. The labels output by the neural network can include but are not limited to the severity of the symptoms, type of the disease and the severity of the disease. In an embodiment, a weighted average of all labels is used to estimate a score for the overall functionality of the user's health for each timestamp. Such a score, though not might not be medically meaningful, could be used as a feature value to train further models, such as those shown in FIG. 8. The predicted symptoms are tagged within the responsible data objects after a verification process. Such data can be used later to further improve the model using semi-supervised or weakly supervised techniques.

Figure 6:
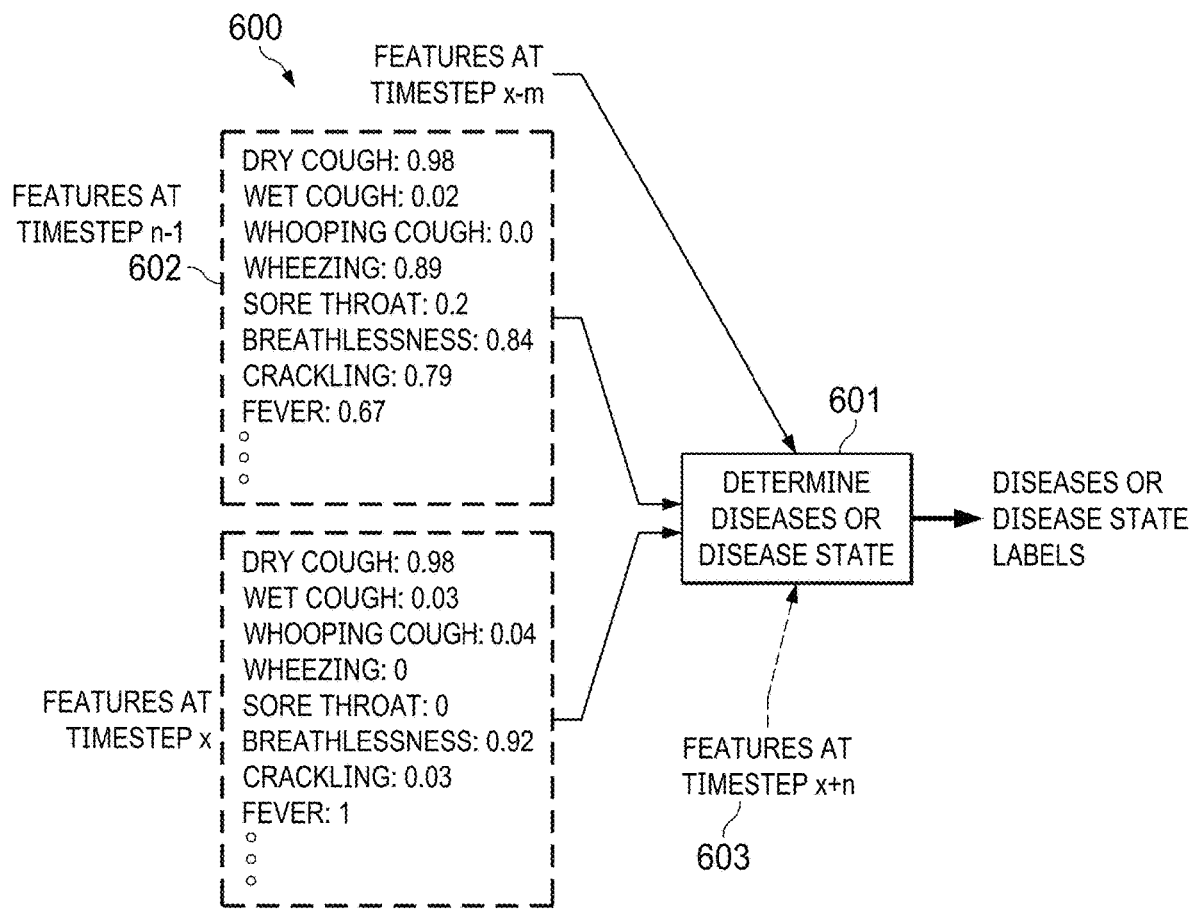
FIG. 6 is a graphical illustration of determining the disease or disease state of a user based on the predicted symptoms of the user at each timestamp using a neural network, according to an embodiment.

FIG. 6 is a graphical illustration of determining the disease or disease state of a user based on the predicted symptoms of the user at each timestamp using a neural network, according to an embodiment. In particular, the method depicted in FIG. 6 describes an algorithm for identifying the disease or the disease state based on the predicted symptoms from FIG. 5.

Figure 7:
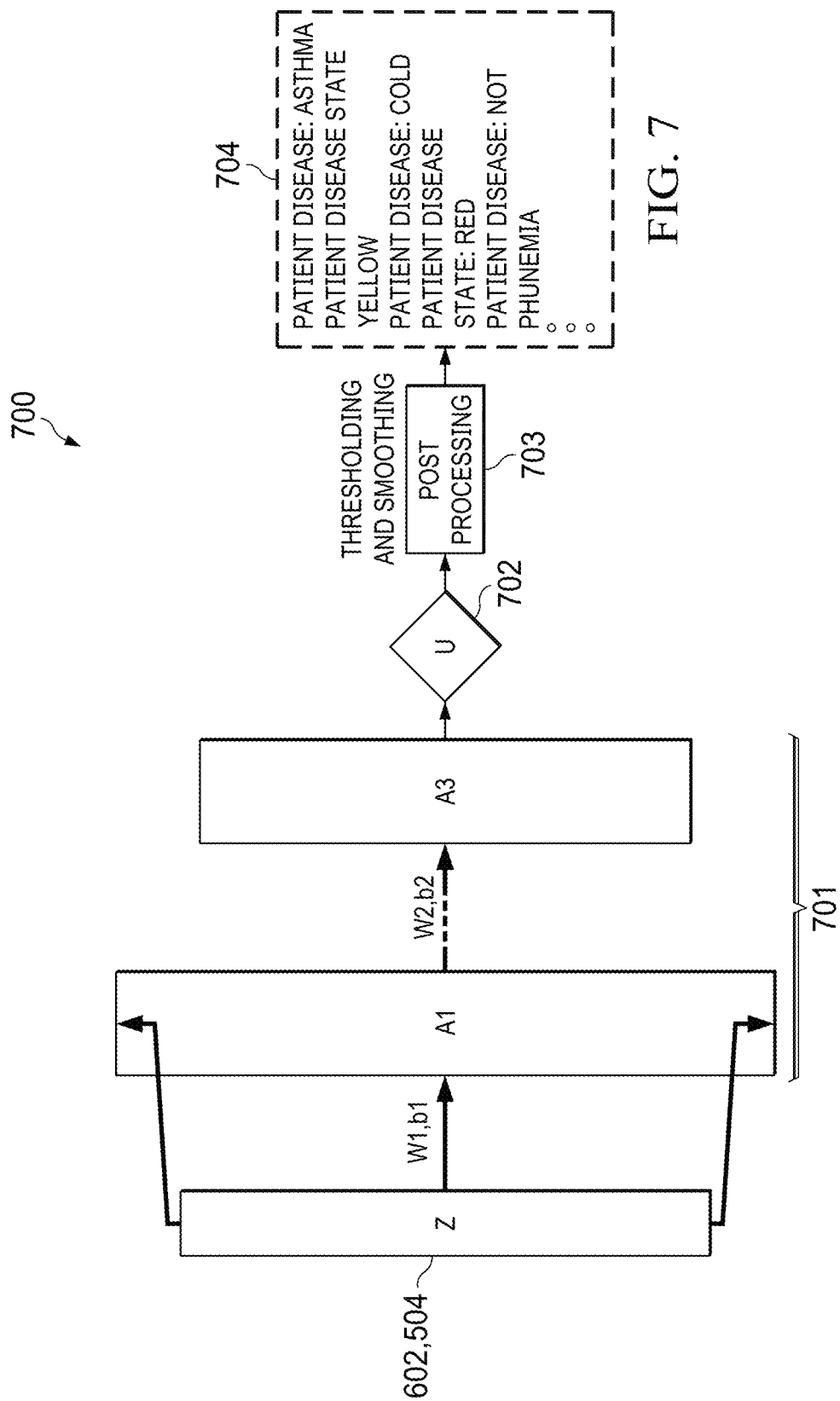
FIG. 7 is a graphical illustration of the disease or disease state determination algorithm using a neural network, according to an embodiment.

In FIG. 7, the method described in FIG. 6 is implemented using neural networks. Based on the predicted symptoms and ground truth labels provided by a physician, a neural network is trained that maps a patient's symptoms to their disease or disease state (704). This network has one or more hidden layers (702). The number of units in the output layers equals to the number of diseases or disease states. The mathematical equations for this network is shown in Equation [5]. The post processing (703) processes the posterior vector through a threshold as follows:

$$U = \theta_2(W_2 * (\theta_1(W_1 * Z + b_1)) + b_2) \quad [5]$$

The relu activation function was used in every hidden layer and the softmax function is applied at the final layer. During training, dropout regularization was used in all layers, except the first and final layer, and the Adam optimizer was used to minimize the cross entropy loss function between the ground truth labels and the predicted values. Once a disease or disease state is determined, the user data objects responsible for determining the disease or disease state are also tagged with this newly available information.

Figure 8:
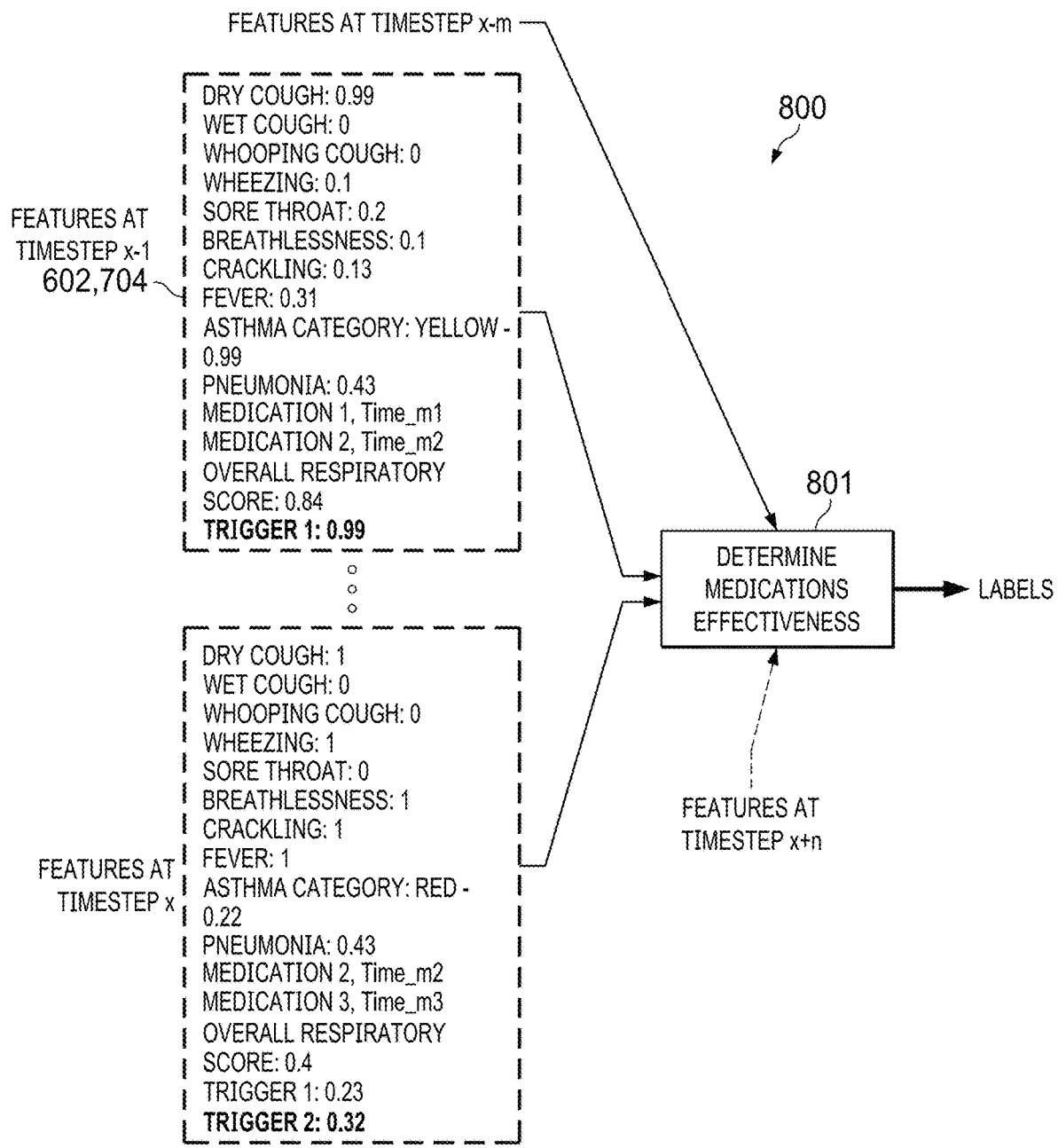
FIG. 8 is a graphical illustration of determining effectiveness of medications taken by the user at each day, according to an embodiment.

FIG. 8 is a graphical illustration of determining effectiveness of medications taken by the user at each day, according to an embodiment. In particular, a method is described for determining the effectiveness of medications in suppressing symptoms or improving a disease state for a user. This information comes from the symptom, disease classifier and a trigger discovery method discussed later. Since medications are not taken at every time step, the feature vectors are marked by the time each medication was taken to also take into account the order and the frequency of taking each medication.

This model learns how physicians adjust a patient's medication given the patient's current and past symptoms and current disease state and its progression, when the patient takes each medication and how frequent, the corresponding symptoms and disease determinations that change after a medication is taken for a period of time and the predicted labels from FIG. 4 and FIG. 6. Once enough data is collected for each patient, a model can be trained to predict: 1) if a particular medication will be effective at lowering patient's symptoms and improve disease state; 2) what time of the day a medication should be taken; and 3) third if a medication should be taken more frequently given the current symptoms. Some medications might have immediate impact and some long term effects. In an embodiment, models that need access to the history of the user's labels are modeled using LSTMs (Long Term Short Term Memory) and recurrent neural networks as discussed later in FIG. 18.

Current disease state and its progression over time and future predictions are fed back to the model as input features to help predict future diseases and states more accurately. For example, it might be more likely that a patient with severe disease state continues being severe as opposed to transitioning from a not so severe state. The model keeps this progression over time and the possible future disease state based on the past and current input feature values, and takes the possible feature values into account when making these predictions.

All identified triggers and potential triggers are then fed back to any of the models discussed earlier as one of the input features to increase the models robustness to false alarms. For example, grass pollen might have been identified as a trigger for a user. If a future weather prediction is a high chance of grass pollen then the input feature vector from the future timestamp contains the likelihood of this possible trigger and its probability as the feature value, so that the model inference is adjusted to take this information into account and help the user prevent potential symptoms.

Figure 9:
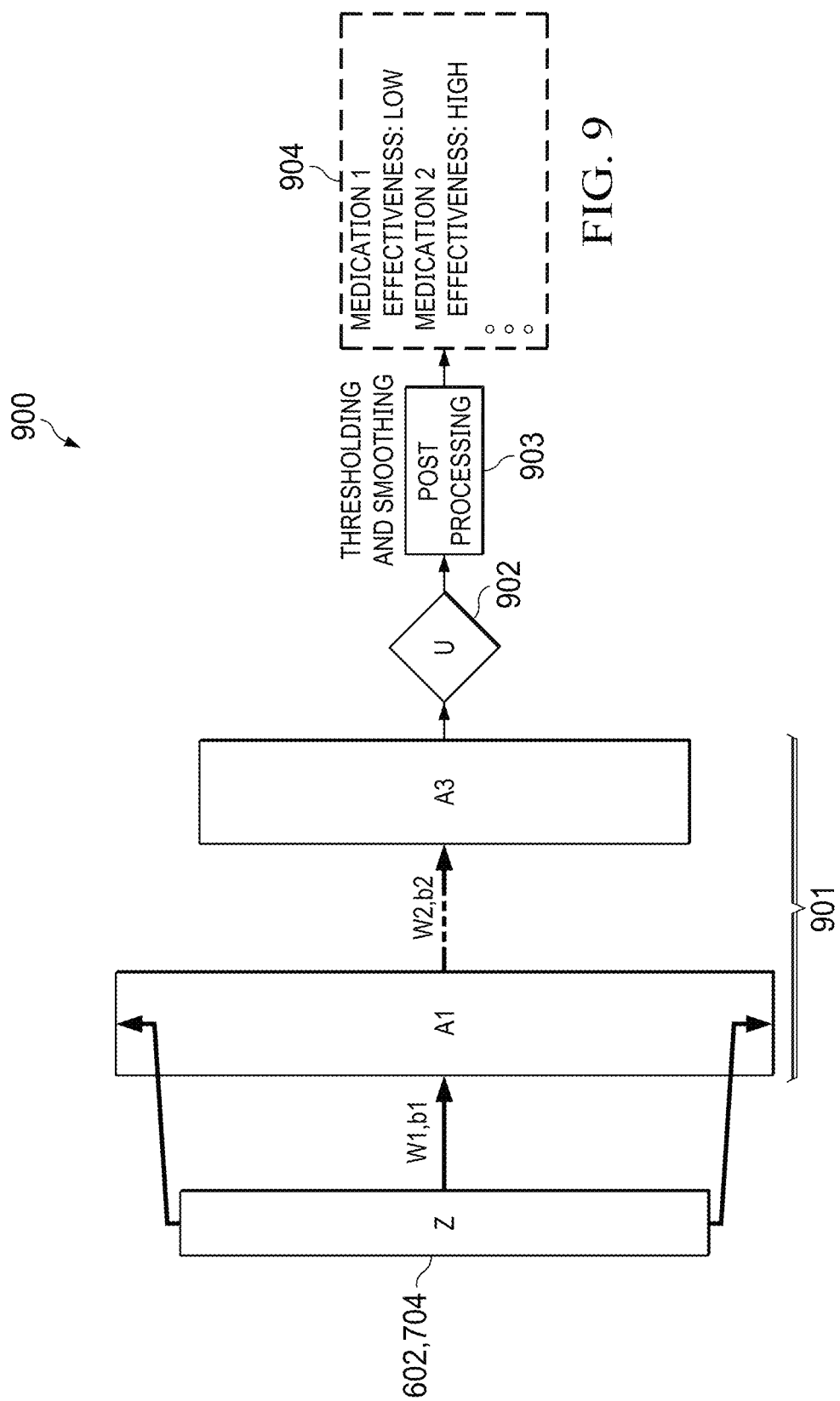
FIG. 9 illustrates a neural network implementation of the method described in reference to FIG. 8, according to an embodiment.

FIG. 9 illustrates a neural network implementation of the method described in reference to FIG. 8, according to an embodiment. In particular, FIG. 9 shows an implementation of FIG. 8 method using feedforward neural networks. Such network is trained and tested similarly to FIG. 5 and FIG. 7. The classification model shown in FIG. 8, however, does not take into account the user's activities and the possibility of a user being exposed to new triggers. That is a user's symptoms might have worsened not because the medication was not effective, but because the physician changed the user's medication, for example due to the user doing heavy exercise or being exposed to smoke. To avoid such issues, the user is first prompted to identify any possible triggers that might have affected the user's health and is taken into account when measuring the medication effectiveness. Overtime the model learns how a physician adjusts the medication based on past triggers and adjusts the medication effectiveness if the trigger presented itself again.

Figure 10A:
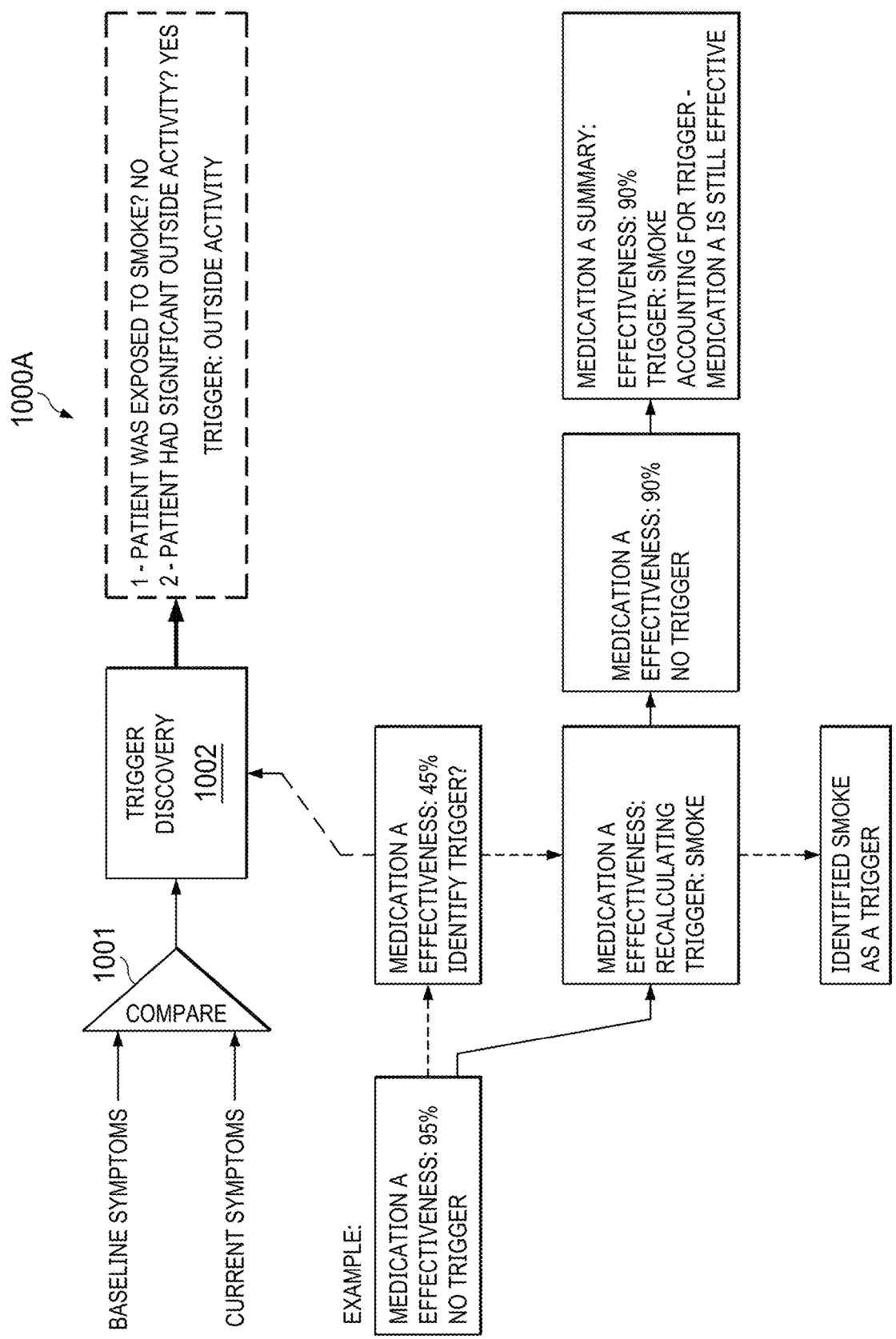
FIGS. 10A and 10B illustrate a trigger identification system/method, according to an embodiment.
Figure 10B:
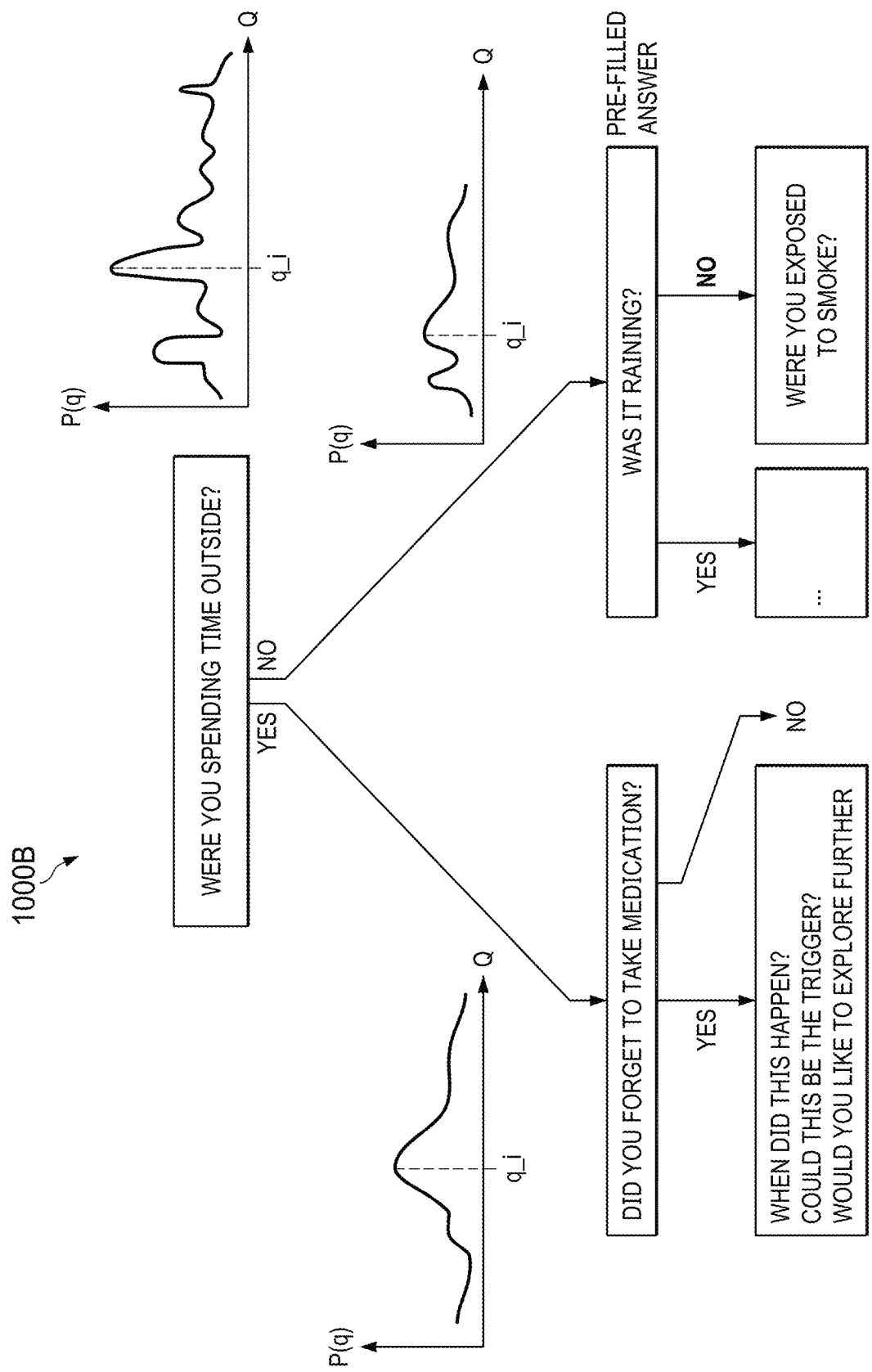

FIGS. 10A and 10B illustrate a trigger identification system/method, according to an embodiment. In particular, FIG. 10A illustrates a method for identifying triggers when the change in the disease, disease state or the symptoms exceed a threshold from the user's usual symptoms. To compare the current symptom with a baseline symptom vector, a distance function (e.g., Euclidean distance) is used. If the distance between the two vectors exceeds a threshold then the user is prompted to identify triggers that might have contributed to the change. Once such triggers are identified, they are tagged (in FIG. 8) to better estimate the medication effectiveness as noted in bold text in FIG. 8. That is, a medication effectiveness is still analyzed if a trigger discovery identified earlier shows that the trigger does not affect the medication effectiveness. The triggers are recorded for each user to help the user keep track of activities that might be aggravating the user's disease state or symptoms. Once a trigger is identified, the newly recalculated medication effectiveness is tagged along with the trigger and the corresponding data object is updated with this information.

An example shown at the bottom of FIG. 10 depicts how the system prompts the user to identify triggers if a medication is not effective anymore to re-evaluate the case. Trigger discovery can be a cumbersome task. It is therefore important to lessen the burden of a trigger discovery on users by asking a sequence of most relevant questions that would result in the shortest path to discovering the relevant trigger. The trigger discovery method (1001) can be trained based on a fixed set of questions that were asked from users for a certain period of time to improve trigger discovery process in the future.

Other types of information metrics such Gini impurity and information can also be used (e.g., CART algorithm). To further minimize the path to identifying the trigger, a decision tree is pre-filled with some of the questions at the time of testing. For example, if a user answered yes to being outdoors then the next question, such as whether it was raining, is pre-filled automatically using the user's zip code at the time of monitoring, if available. The user can therefore skip this step and answer the next question. In the event the system was not able to find a trigger for the cough, the user is prompted to find the trigger manually. This information is then used to further optimize the decision tree. Note that discovering triggers this way would not count as a classification task, but rather as a task of finding which features should be requested and when to minimize the path to identifying a trigger.

For example, consider a case where a user's true trigger was spending too much time outside in the rain. To discover the possible triggers, a user might be asked if he has had any significant outside activities. The user may then be asked another question, such as forgetting to take medications. The user might spend over ten minutes to find out that spending too much time in the rain was the trigger. A shorter path to discovering rain as the trigger could have been made after asking if a user has had significant outside activities given the weather information can be accessed automatically from numerous sources.

Figure 20:
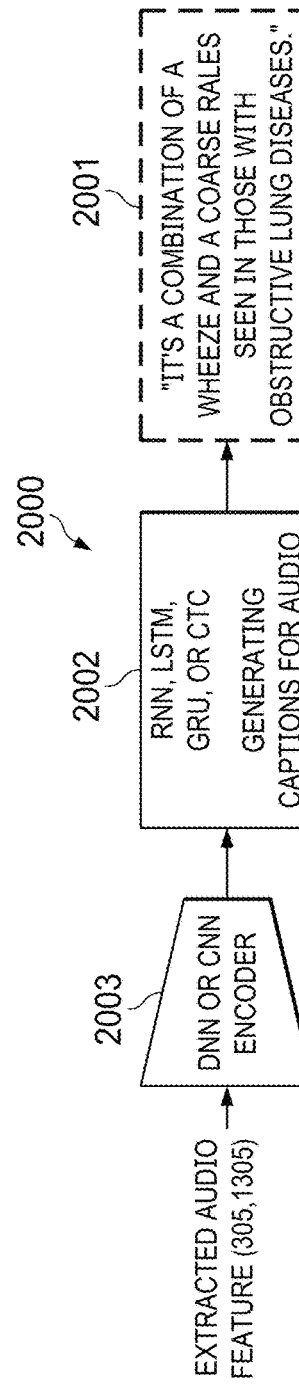
FIG. 20 illustrates a method of generating a caption for an audio signal, according to an embodiment.

To learn which questions should be asked first and in which order to discover triggers more quickly, a learning algorithm such as a decision tree can be used as shown in FIG. 20. A decision tree is first trained on a collection of data similar to the following example: answers to a fixed set of questions from each user in a Boolean format (e.g., 1 or 0) along with predetermined features for each user such as a user's symptoms, weather for the zip code at the time of monitoring, etc., and a label corresponding to this feature set which is the identified trigger. Notice that throughout training one might identify that some question or predetermined features do not add or add very little value in finding the trigger. And since decision trees are highly interpretable models, questions can be designed carefully to make sure the path to identifying a trigger is as short as possible. These questions are used as input features to the decision tree and the final triggers are used as the output labels. During training the features that would contribute to the lowest uncertainty, or biggest information gain, are selected to represent the question at that step. During testing, questions are asked in an order that minimizes the average entropy or the uncertainty as defined by the training process earlier. Entropy was defined earlier in Equation 4.

Figure 11:
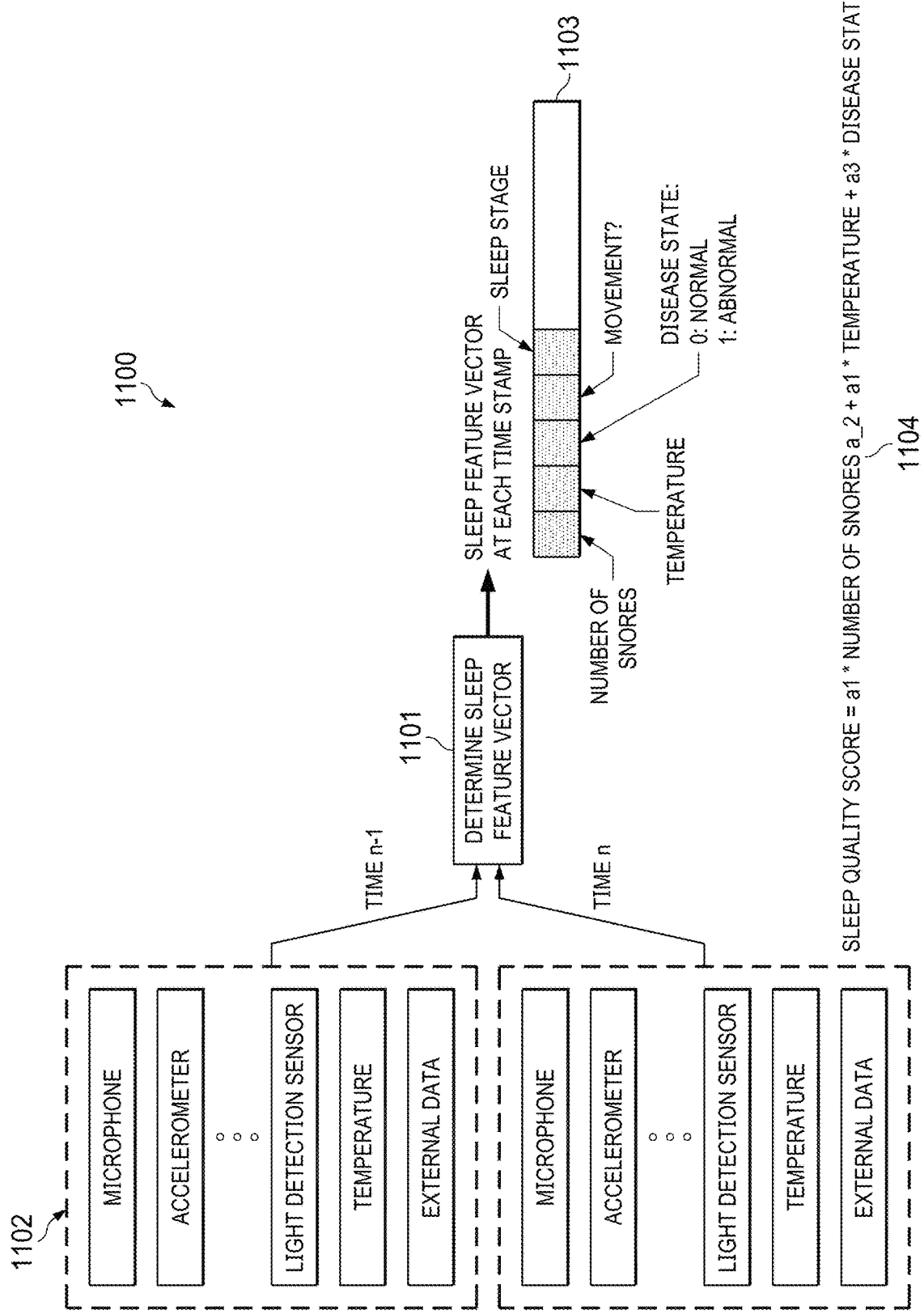
FIG. 11 illustrates a method of determining a sleep score of a user, according to an embodiment.

FIG. 11 illustrates a method of determining a sleep score of a user, according to an embodiment. In particular, as shown in FIG. 11, one or more microphones can be used to detect snoring, teeth grinding or other related audio events (e.g., gasping for air) and an accelerometer and RF to measure and analyzes user's movement and respiration rate and other sensors for measuring other related symptoms as needed. Training a model to detect such events is similar to the training described in reference to FIG. 4 and as shown in FIG. 12A.

In some cases, the user's sleep quality can be correlated with the user's disease state and symptoms. For example, if the temperature in the user's bedroom increases the user starts coughing or showing other symptoms. In such a case, a sleep score can be determined based on a weighted average of user's symptoms, so that a user can take actions that could increase their sleep quality. To determine the sleep quality sleep scores, a series of features that could describe the sleep quality (i.e., a sleep quality feature vector) can be extracted at each timestamp.

Figure 12A:
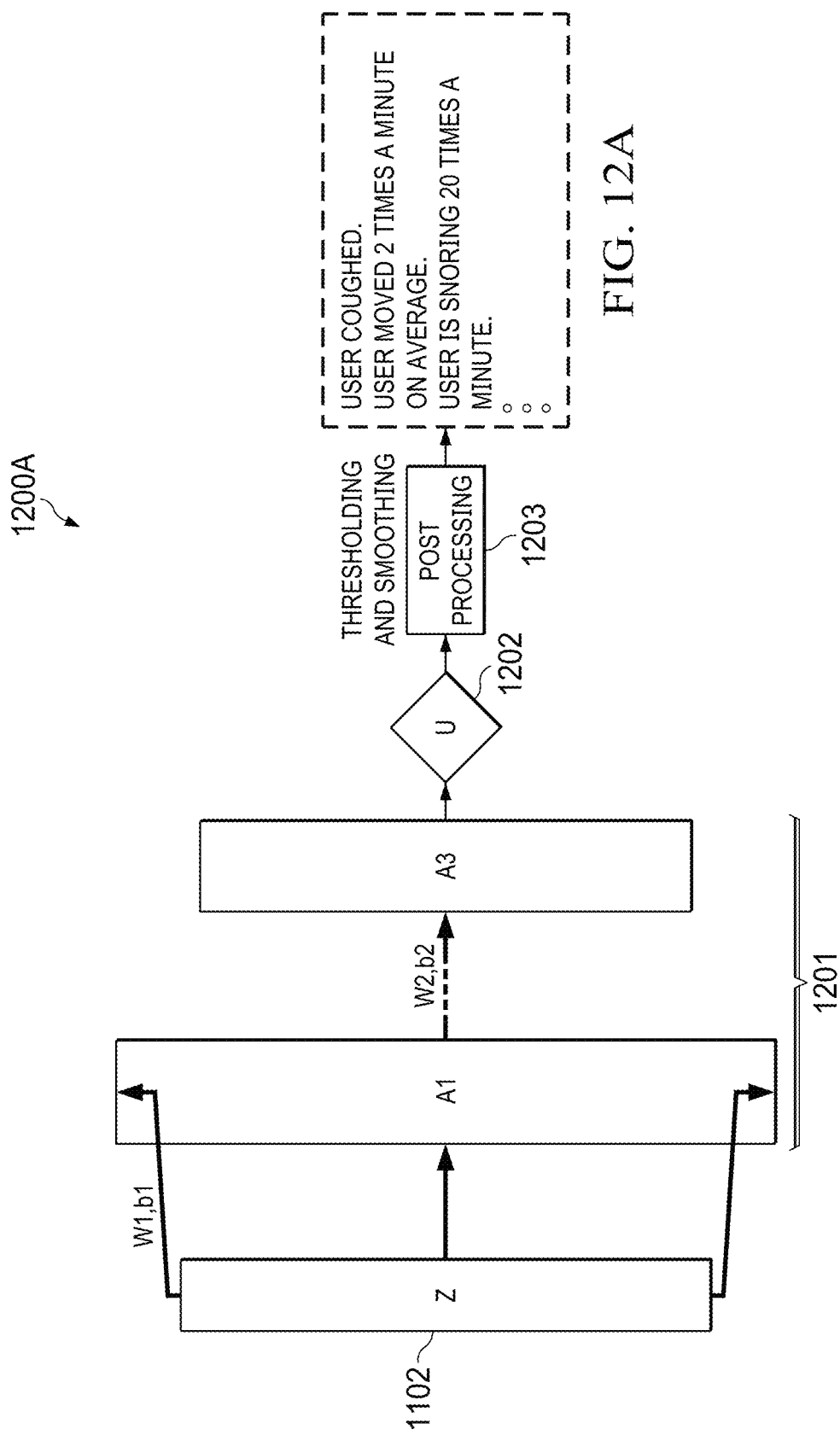
FIG. 12A illustrates a neural network implementation of the method of FIG. 11, according to an embodiment.

FIG. 12A illustrates a neural network implementation of the method of FIG. 11, according to an embodiment. As shown in FIG. 12A, such method is implemented using a neural network, where the neural network is first trained on labeled data that are collected from users over time. Similar to the methods shown in FIG. 5, 7, or 9, a feedforward neural network is trained on the labeled data that accepts features from a number of sensors and predicts a number of features, including but not limited to: sleep stages, audible symptoms, excess movement, possible sleep disorders, etc. For example, an accelerometer or an RF transceiver can be used to detect movements in the bedroom, and a thermometer can be used to detect the temperature in the bedroom. For example, if the change in movements is more than a threshold, then one of the elements in the feature vector is set to 1 to show the excessive movement (1103) or assign a sleep stage (e.g., REM) based on their predicted symptoms. More traditionally, PSG sensors such as Electroencephalography (EEG), Electrocardiography (ECG), Electromyography (EMG), and Electrooculography (EOG) can be used to track a user's brain activity, heart rhythm, muscle activity, and eye movement respectively. PSG sensors can be used to monitor the patient's body, though it comes at the cost of the patient being connected with several wires which would negatively impact the patient's sleep quality, which may result in less accurate data. In addition, since the feature vector is extracted from all sensors for each timestamp, the symptom detection scheme discussed earlier can be expanded to detect more vitals and symptoms that are needed for a sleep study. Such models can be used to make PSG scoring more efficient, accurate, and consistent help validate technicians manual scoring.

Once a sleep quality feature vector is determined, a sleep quality score can be determined based on a weighted average of the feature vector (1104). However, determining the coefficients of such averaging is not obvious (a_i parameters in 1104). For example, some users might tolerate variation in the temperature more than others and yet have a better sleep quality. As such, a sleep quality score is a personal score for each user. A sleep score is first determined by the user adjusting their sleep quality score based on their experience and a generic number determined by an algorithm based on the detected symptoms. A regression model can then be fitted to the feature-symptom space to find the coefficients that best fit the curve. Once a sleep quality score is determined, the user data objects responsible for that score are also tagged with the sleep quality score. For example, the information is tagged in the user data object so it can be used to better predict the user's symptoms, disease or disease state and their sleep quality.

Figure 12B:
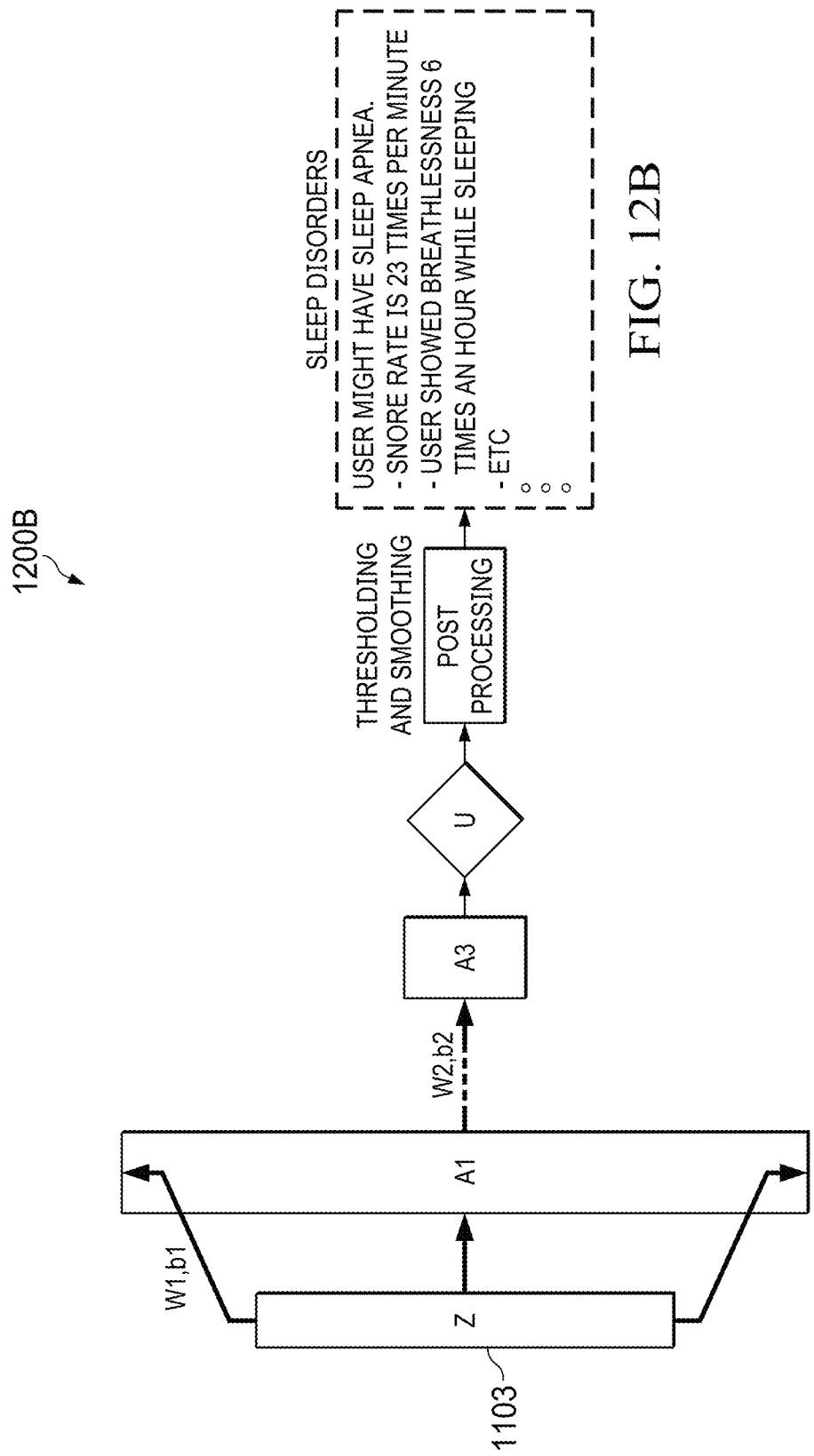
FIG. 12B illustrates a network for determining sleep disorders, according to an embodiment.

FIG. 12B illustrates a network for determining sleep disorders, according to an embodiment. In particular, FIG. 12B depicts a method for identifying a sleep disorder based on the sleep feature vector (1103). A neural network is first trained on this set of features wherein the labels are sleep disorders, such as sleep apnea and insomnia and the corresponding type, etc. Note that a patient may be suffering from several sleep disorders. As such, the model can be tuned to predict a sleep disorder at every epoch (i.e., a fixed duration of time). Such results can then be used to treat each disorder more effectively as they may be triggered by different causes and trend over time in different ways. The trigger discovery scheme discussed earlier can be used to find the cause for each sleep disorder. As discussed later, a set of actions can be recommended to the patient based on their symptoms and data to improve user's sleep quality. In an embodiment, the classifier can be modeled with a logistic regression model or a neural network as discussed earlier.

Figure 13:
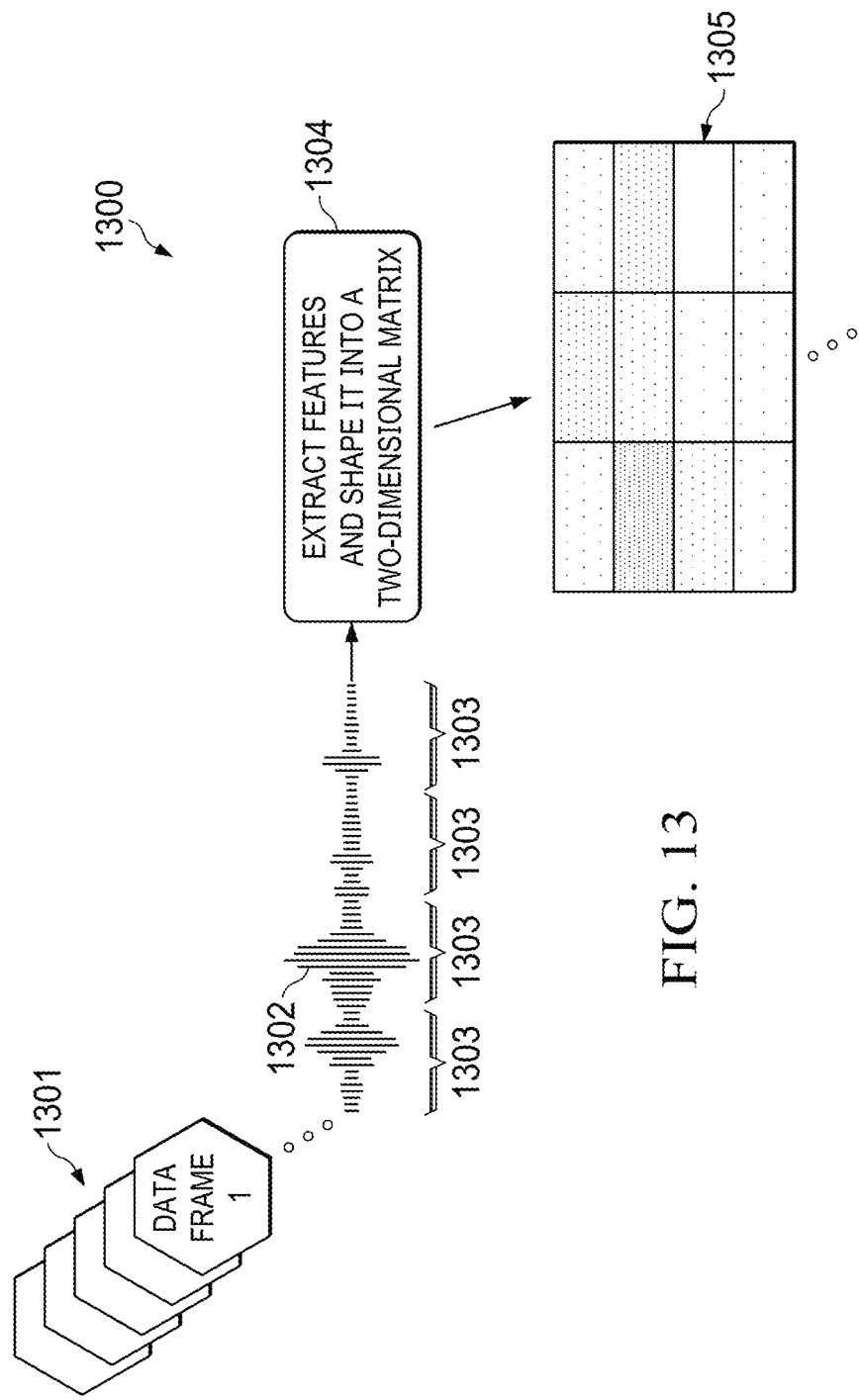
FIG. 13 illustrates a feature extraction technique for convolutional neural networks, according to an embodiment.

FIG. 13 illustrates a feature extraction technique for convolutional neural networks, according to an embodiment. In another example embodiment, the features extracted from each sensor at each timestamp is fit into a matrix (1305) instead of concatenated together into a feature vector as previously described in reference to FIG. 3 (305). An advantage of not vectorizing the features is that the neural networks can see features from different sub-frames in their true order. A CNN can replace any of the feedforward neural networks shown in FIGS. 5, 9, and 12, as long as the extracted features are showing some temporal patterns. For models such as the one shown in FIG. 9 wherein sub-frames are not clearly defined, a CNN can still be used if the past, current, and future features are fit into a matrix wherein each column could represent a feature from a particular timestamp.

Figure 14:
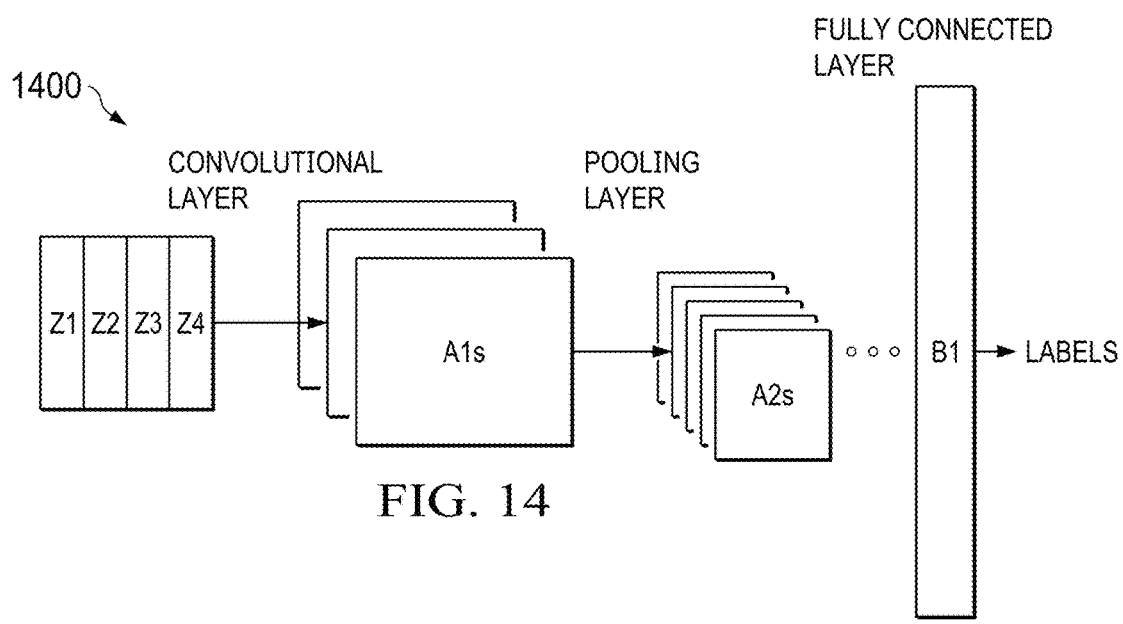
FIG. 14 illustrates a convolutional neural network as a classification algorithm that employs the extraction technique of FIG. 13, according to an embodiment.

FIG. 14 depicts a CNN as a classification algorithm that employs the extraction technique of FIG. 13, according to an embodiment. FIG. 14 depicts a CNN that employs the feature extraction shown in FIG. 13. Training a CNN is done similarly to training feedforward neural networks with the addition of more parameters to adjust, such as striding parameters, type and number of pooling layers, size of each filter, etc. CNNs are usually followed with one hidden layer, one or more fully connected layers as the final layers, and a softmax layer when used for classification purposes.

Figure 15:
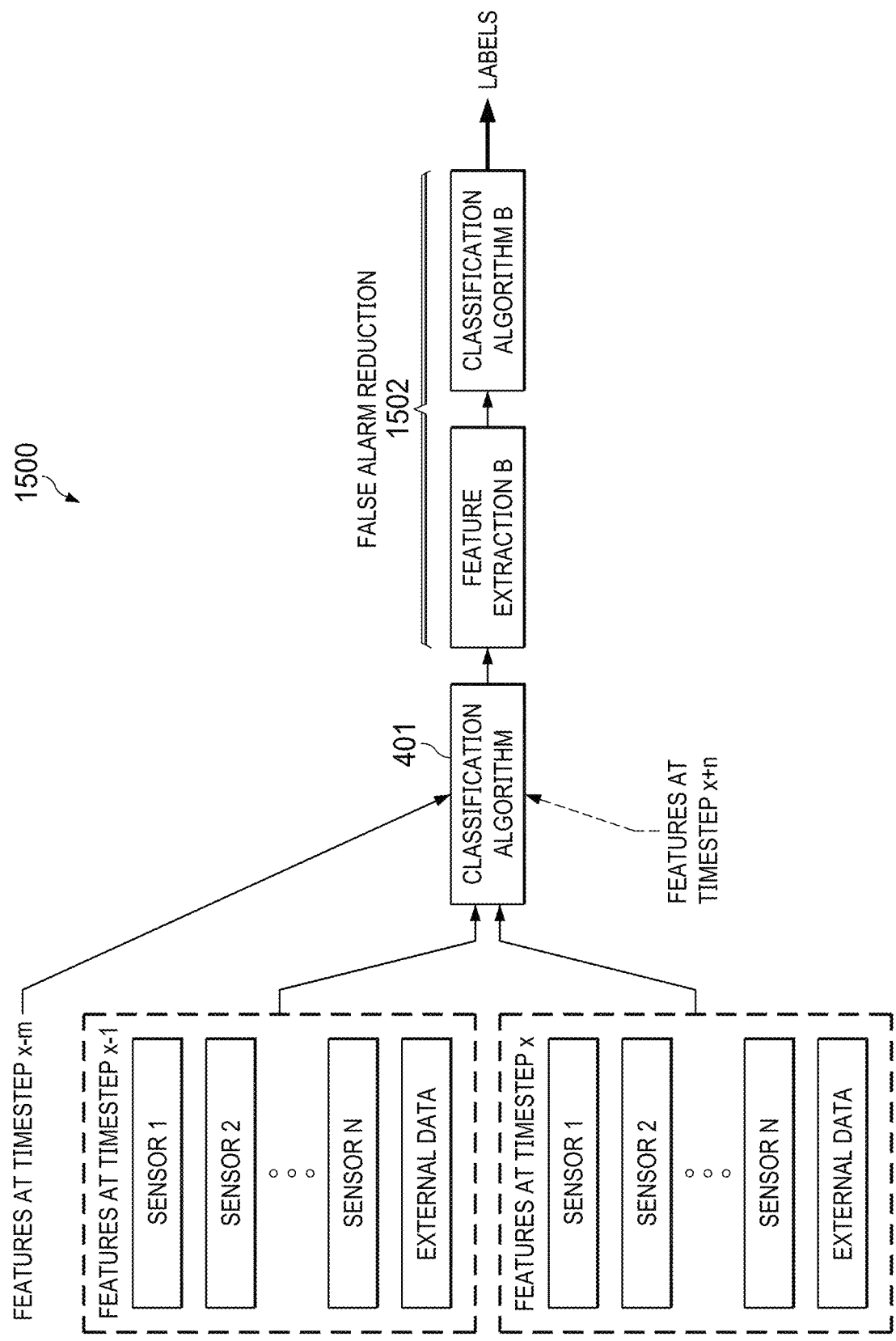
FIG. 15 illustrates a method for reducing false alarms by increasing the precision of the algorithm described in reference to FIG. 14, according to an embodiment.

Almost all classification algorithms are prone to incorrectly predicted labels that are false positives. To suppress false positives, various heuristic and sub-heuristic methods can be used to cover different corner cases. However, heuristic methods usually fail in practice and even hurt the algorithm's precision. FIG. 15 illustrates a method for reducing false alarms by increasing the precision of the algorithm described in reference to FIG. 14, according to an embodiment.

Referring to FIG. 15, an additional classifier is used that is trained with possibly different sets of features and a different analysis window, and that uses only predicted samples from a first classifier to detect if a prediction from the first classifier is a true positive or a false positive (1502). Such features may differ from the features extracted from the first network. The timestamps of the second stage classifier could be longer or shorter than the first stage or a combination of both, so that it can observe other aspects of the data that were not captured in the first stage sub-frames. The advantage of using a second classifier learning from the first stage is that the second classifier learns what features are generally more important and the possibility of overfitting is lower than using manual heuristics. Such classifiers can also learn to be more personalized for a specific user through model concatenation. For example, one of the models can learn what the true positives and false positives for a specific user are and further filter the result coming from the earlier stages.

Figure 16:
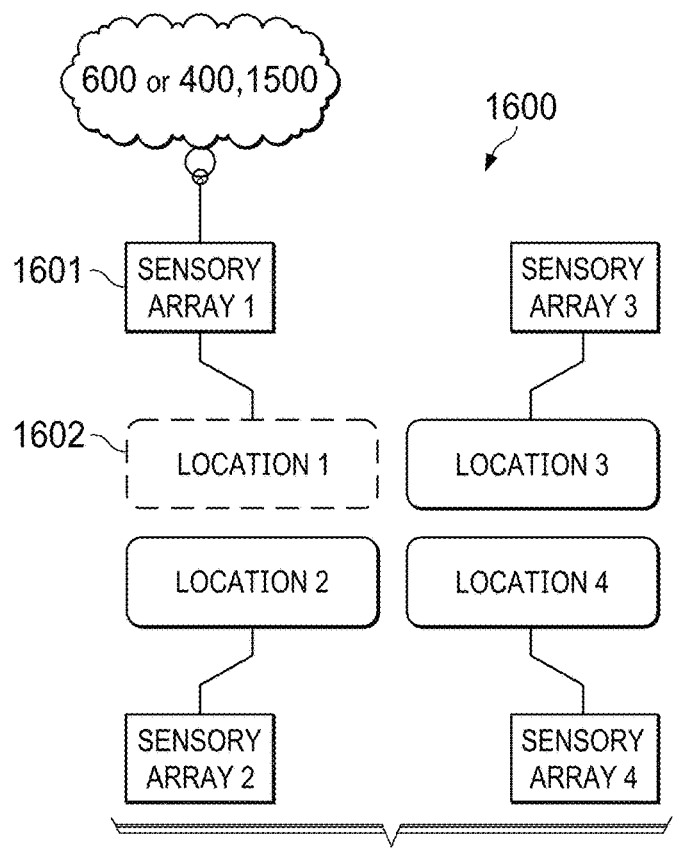
FIG. 16 illustrates a method for tracking respiratory health of a population, according to an embodiment.

FIG. 16 illustrates a method of tracking respiratory health of a population, according to an embodiment. The example embodiment discussed in FIGS. 4, 6 and 15 can also be applied to determining the density of respiratory events, disease or disease state for a population (e.g., students in a classroom, people riding public transportation, passengers in a vehicle, etc.). For example, consider the scenario where a number of sensory arrays (1601) are collecting audio data in a classroom from different spots (1602) in the room through beamforming techniques, such as the techniques described in (http://externe.emt.inrs.ca/users/benesty/papers/aslp mar2007.pdf), wherein each array is only monitoring one fixed location and no other locations. If the number of respiratory events (or the severity of the disease or the disease state corresponding to users in that location predicted by one of the mentioned methods) exceeds a certain threshold at a certain location in the room (e.g., 1602), then an authority can be informed to monitor the situation more closely to avoid spreading a respiratory disease (e.g., the flu) in the whole classroom or even throughout the school and surrounding community. In another example, if the number of respiratory events from a certain location have not passed a predetermined threshold but corresponds to a certain infectious disease, then the authority is informed to investigate the situation further. Such information, in addition to other collected data such as the time of day, weather, or any particular event happening, provides valuable information to the authorities that can be used to prevent the spread of respiratory diseases, such as flu, cold, etc. Such information can also be used to monitor the trends of respiratory diseases from different locations, so that authorities can prioritize actions appropriately.

In another embodiment, sensors embedded in a vehicle such as microphones and other external sensors (e.g., a camera facing the driver and the passengers) can be used to monitor the driver's health and passenger safety by monitoring the driver's attention to the road. This not only provides additional useful information about the patient's respiratory health in a different environment, but it is also helpful in predicting strokes and seizures in patients with previous incidents. A patient can be alerted about a possible incoming stroke or seizure attack if an abnormal breathing pattern related to such attacks is detected, and take actions as needed. As such, the collected data from the sensors can be connected to any of the former schemes described above for feature extraction and any of the former models described above can be expanded to predict more symptoms and diseases as well as the driver's attention to the road.

Figure 17:
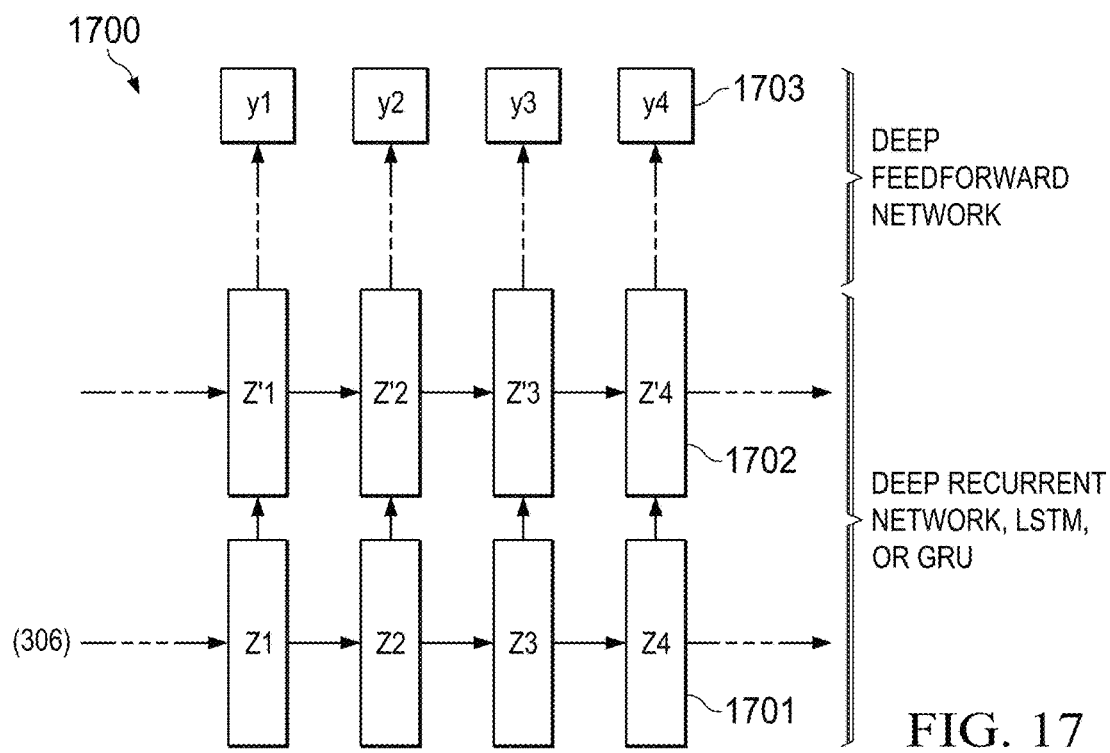
FIG. 17 illustrates a recurrent network for predicting respiratory data from time-series features, according to an embodiment.

FIG. 17 shows a recurrent network for predicting symptoms from a sequence of data according to an embodiment. In particular, FIG. 17 depicts a recurrent neural network (RNN) for predicting respiratory or sleep abnormalities based on the features extracted from FIG. 13 or FIG. 3A/B from each timestamp. The layers in the bottom (1701) of this figure represent these features rolled in time. Layers labeled Z'1 (1702) can be set to any memory units such as Long Short-Term Memory (LSTM) or Gated Recurrent Units (GRUs). Only one recurrent hidden layer was used to train this example RNN, as training RNN with over one hidden layer is computationally expensive. A deeper feedforward neural network, however, can be used as a final layer to predict labels, where the labels are set during training when a symptom starts and unset when the symptom ends. This type of RNN network is an example of a many-inputs-to-many-outputs architecture. A many-inputs-to-one-output sequence can also be designed, wherein the label is only set once for each corresponding symptoms. As mentioned earlier for the previous feedforward neural networks, an RNN model is first trained offline using back propagation. Once the model is trained, parameters are fixed during inference. In another embodiment, the input feature can be compressed using a one dimensional convolutional neural network before entering the memory cells as it decorrelates input features further and adjust label vector dimensionalities to any desired value.

Figure 18A:
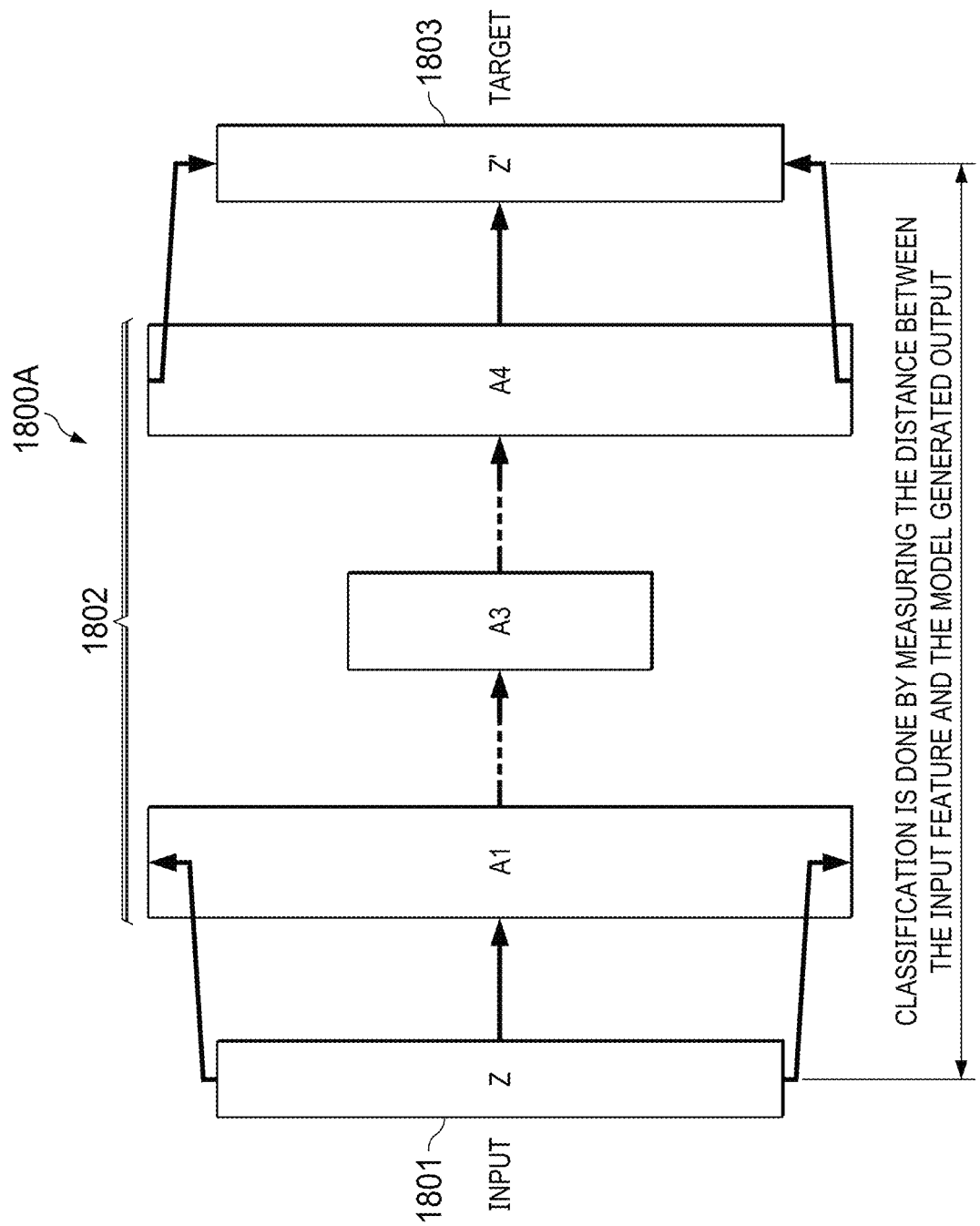
FIGS. 18A and 18B illustrate a method of using generative models, such as auto encoders as classifiers, according to an embodiment.
Figure 18B:
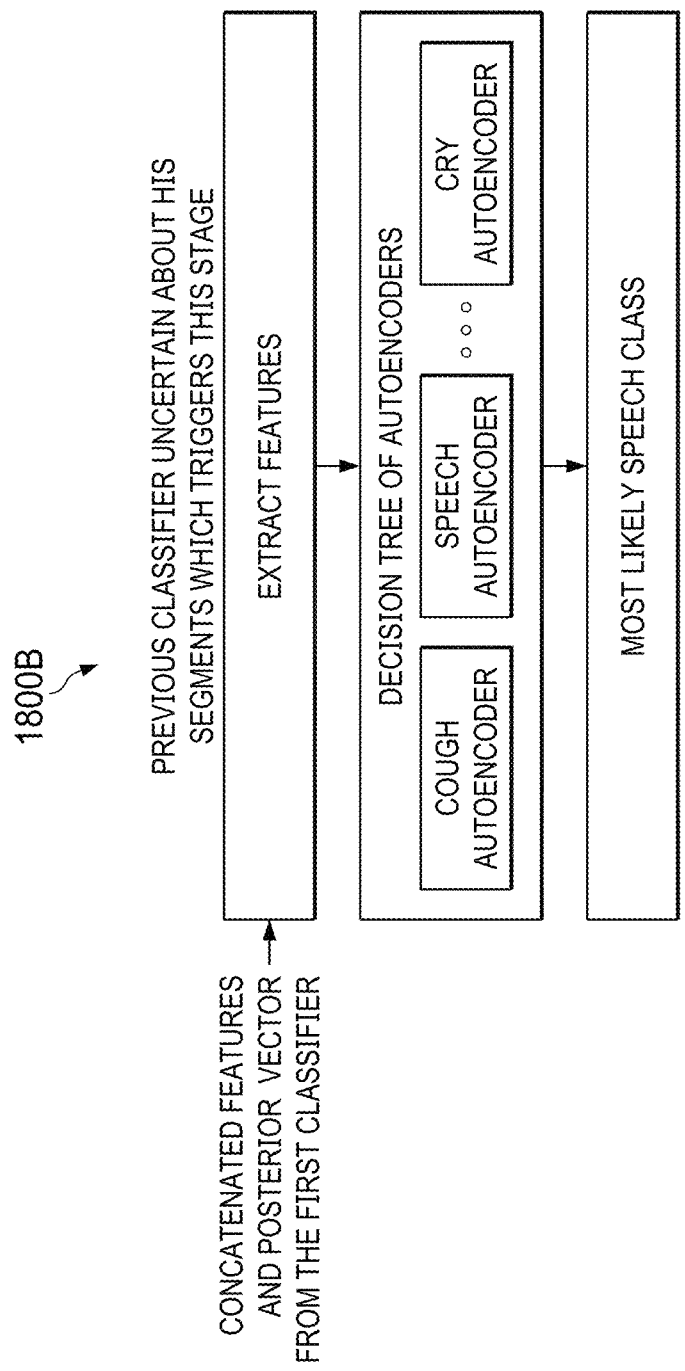

FIGS. 18A and 18B illustrate a method of using generative models such as autoencoders as classifiers, according to an embodiment. In another embodiment, autoencoders are used as a generative model for classifying symptoms. Several autoencoders can be trained for different classes, such as speech, coughs, wheezing, noise, crying, etc. As depicted in FIG. 18A an autoencoder (1802) is trained on a feature vector corresponding to an input data and a target label (1803). Once such autoencoders are trained, they can be applied to segments wherein the previous classifier was uncertain about. The distance between the output of these classifiers is then measured as shown in FIG. 18B. For example, consider a segment passed through a cough autoencoder and resulting in a large distance, more than a predetermined threshold, between the input and the target. That means the autoencoder is unable to generate that segment and therefore it is most likely not a cough. Since there can be several autoencoders, a decision tree can be trained to identify which auto encoder and in which order they should be applied to verify the true label of segments more efficiently.

Any of the previously discussed models can also be improved with the newly found data about the user, e.g., user's symptoms severity on rainy days. To improve an existing model, most of the layers except the last few layers are fixed as they tend to capture more high level and data specific features. Such technique is also known as "transfer learning" in the literature and is used often when the quantity of the data is not enough, but an existing model can be adapted to learn from a smaller dataset by "personalizing the model" to that dataset while taking advantage of the previous model learnt lower-level features.

Figure 19:
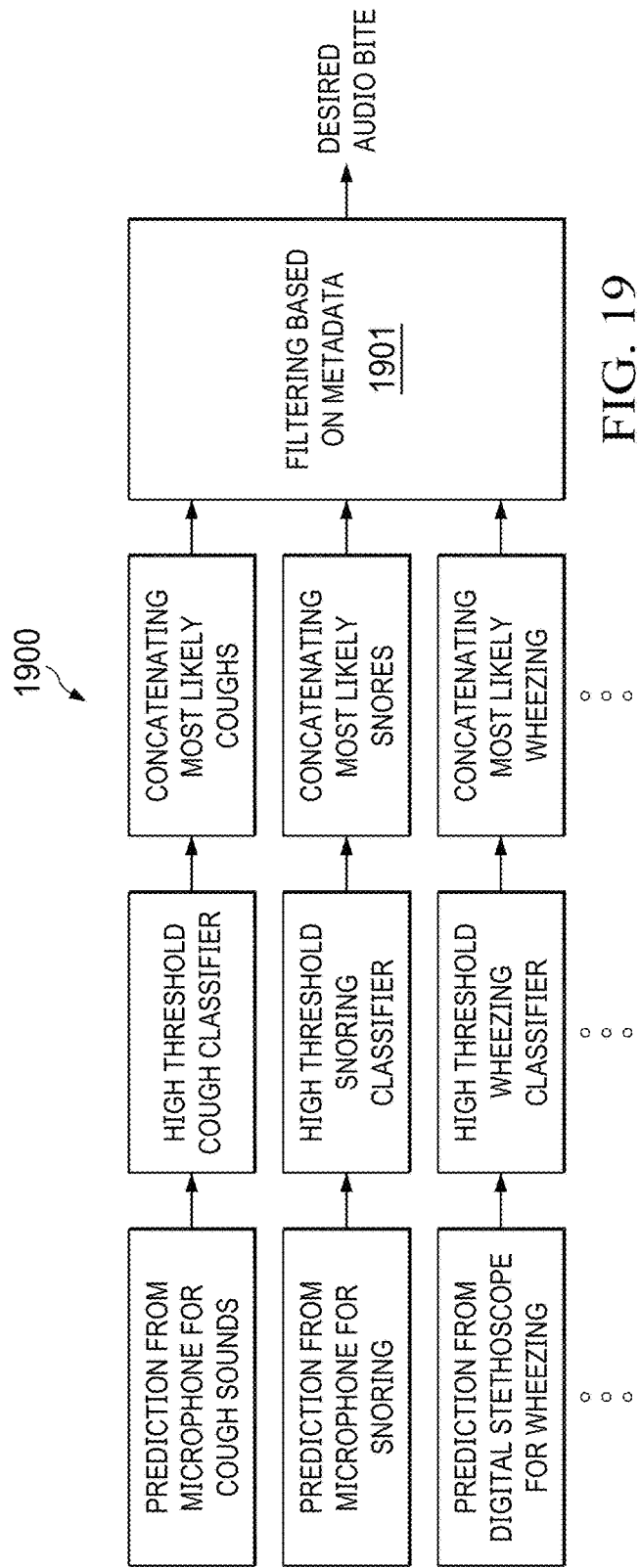
FIG. 19 illustrates a method of creating a meaningful summary of symptoms captured by audio sensors, according to an embodiment.

FIG. 19 illustrates a method for creating a meaningful summary of symptoms captured by audio sensors as an evidence to a user, according to an embodiment. As discussed in the background, listening to audio signals captured by different sensors can be useful to a physician in making a decision about symptoms, disease or disease state as well gaining user's trust that the model prediction is accurate. However, listening to hours or even several minutes of audio is inefficient and won't do any good in practice. In an embodiment, the predicted audio corresponding to each sensor and symptom is passed through a second classifier with higher thresholds, so that only a smaller yet diversified portion of the collected audio signal is presented as a summary of all audio recording for a particular symptom as shown in FIG. 19. A physician may also filter a current sound bite for a specific symptom by the disease or the disease state, time of occurrence, type of sound event, etc. to create the desired audio bite (1901) that is most representative of what the physician's hypothesis. For example, in FIG. 6 if the disease state was determined to be uncontrolled, new metadata is added to the data object (104) as an uncontrolled disease. As such, when concatenating the audio recording in FIG. 19 these metadata are used to filter the sound bite further.

FIG. 20 illustrates a method of generating a caption for an audiobite. In another embodiment, a classification scheme such as DNN or CNN can be used to encode an audio signal to a descriptive feature vector (i.e., the extracted features from the audio signal e.g., $A_3$ in FIG. 5, $B_1$ in FIG. 14). Such an audio captioning system is depicted in FIG. 20. Once a feature vector is produced (2000), it can be fed to an RNN (or LSTMs, GRUs, or a Connectionist Temporal Classification (CTC)), which produces a caption describing the content of the audio signal (2001). Such a model is trained on descriptive features as an input to the model and a sentence provided by a physician or an annotator describing the content of the feature using a recurrent neural network. A technique was previously applied to image captioning in Oriol Vinayls paper, et. al., "Show and Tell: A Neural Image Caption Generator." In this paper, the labels contained descriptions of the image and where different objects are located. For audio signals, and more specifically audible events, the caption could, for example, describe the patient's lungs. An example caption could read: "This breath sound seems to be a bronchi in most of the recording; a harsh sound representing sputum in the upper respiratory tract." (2002). As another example, such systems could be used to warn authorities. An example caption could read: "a younger female screaming and asking for help." Such audio data can be described by multiple physicians to provide additional labels for each audio signal. An RNN (or LSTM/GRU network) can then be trained on these labels to generate such captions for new audio data based on the encoded feature.

In another embodiment, personalized detection of symptoms can be used where no/minimum data from one patient is available. Consider an example scenario where multiple patients with symptoms are in a room with one monitoring device. The goal is to monitor all patients using one device. There are multiple problems that can present themselves in this scenario. The monitoring device is listening to all sounds and does not use any spatial cues that can localize the patients using techniques such as beamforming as they are statistical models with their own limitations. The number of patients in the room can also change and the algorithm needs to adapt to incoming patients. To make this matter more difficult, a new patient might only have a few data samples which makes it hard to train a large networks that performs multi-class classifications on the same symptom uttered by different patient wherein the contents of classes are very similar to each other, e.g., class one represents patient A coughs and class two patient B coughs. The proposed personalized detection of symptoms can tackle all these problems using one monitoring device using only one microphone.

Figure 21:
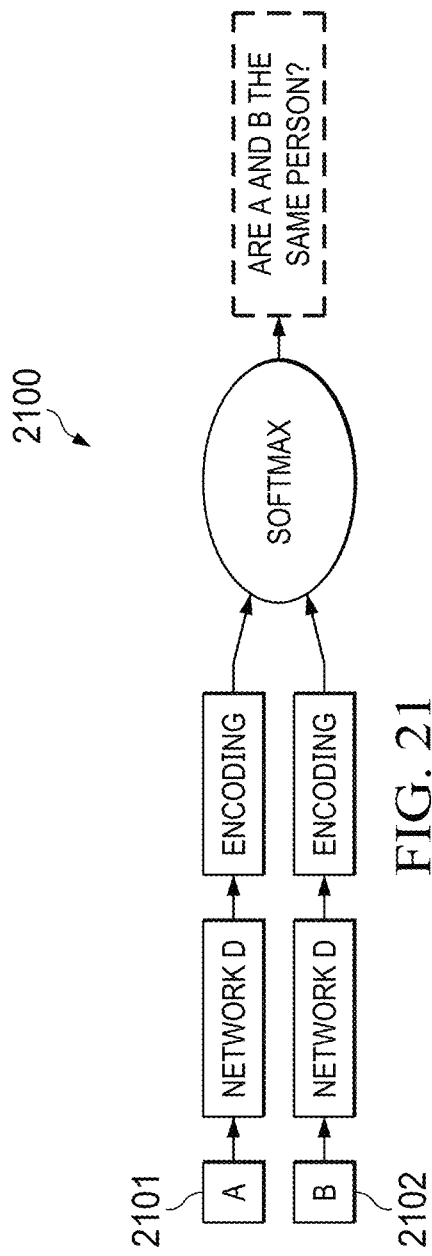
FIG. 21 illustrates a neural network that is trained to make a decision on whether the encoding of multiple sets of symptoms belong to the same person, according to an embodiment.

Referring to FIG. 21, a network (2100) is trained that makes the decision on whether the encoding of symptoms shown as A (2101) belongs to the person with the encoding of symptom B (2102). As shown in Equation [6], the network predicts y=1 if the symptoms belong to the same person and 0 otherwise, wherein σ is the sigmoid function, and k is the training example k and i refers to the element i in the encoding vector.

$$y=\sigma(\Sigma_k W_i(A^i_k - B^i_k)+b) \quad [6]$$

In order for this network to converge, the choice of encoding is an important choice. These encodings can be learned from the neural network using techniques such as one-shot learning or Siamese network. In such networks, there are three inputs, a reference respiratory sample, a positive sample from the same person, and negative samples from a different person which has similar characteristics to the reference person but that originated from a different person. The output of this network is an encoding vector that represents the features of the reference person's symptoms. A nice property of this feature is that it is maximally discriminated from the same symptoms originated from a different person yet clustered closely with the ones from the same person. Such network can be trained on a loss function which is the addition of the difference between norm 2 distance between the reference and positive example from the norm 2 distance between the reference and the negative example as shown in Equation 7:

$$L(R,P,N)=(\|f(R)-f(p)\|_2^2+\|f(R)-f(N)\|_2^2+\alpha,0), \quad [7]$$

wherein R, A, and N stand for reference, positive, and negative examples, respectively, f denotes the encoding of the samples found from the encoding layer and a is a constant set to 0.4 to avoid the loss function from creating zero embedding vectors.

Figure 22:
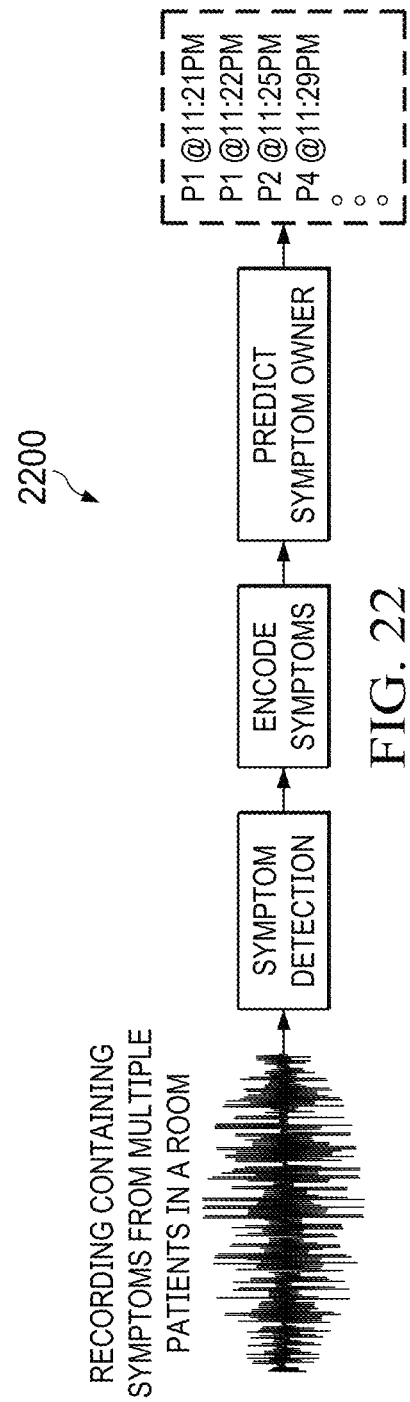
FIG. 22 illustrates a neural network that learns symptoms for multiple patients in a room and predicts which patient owns a particular set of symptoms, according to an embodiment.

The mentioned techniques implemented by Equation 6 and 7 tackle the aforementioned issues as follows. A few dozens of samples from each patient is used to predict (using Equation 6) an embedding vector for each patient and then a similarity function is learned (using Equation 7) by minimizing a loss function for a symptoms that belongs to the same patient and those that are not. As such this network learns the difference between patient's symptoms and can track their symptoms individually as shown in FIG. 22.

Figure 23:
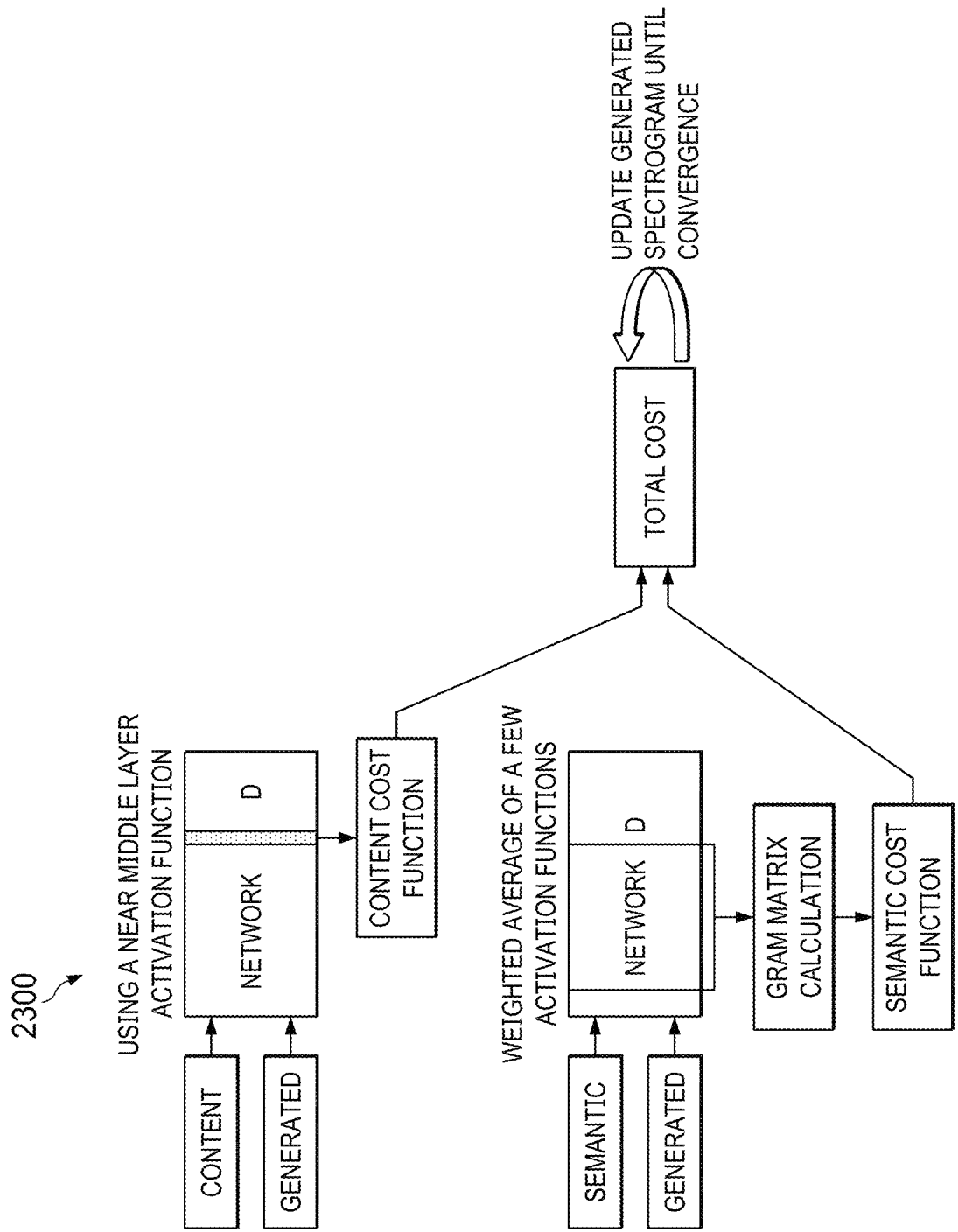
FIG. 23 illustrates a neural network based feature augmentation technique, according to an embodiment.

Referring to FIG. 23, an augmentation techniques for creating realistic, but synthesized features is shown. For example, consider a feature vector describing a 5 years old female cough sound. This feature can be augmented using the proposed technique to describe the patient's cough sound when the patient is in pain, in a noisy environment, or far from the monitoring device. This feature can also be transformed to describe another patient who might be of a different gender, age, or have a different disease. To describe the feature augmentation technique, consider an example where the features consider an audible symptom represented in a time-frequency domain with a grid size 64 by 500 for every one second of data. Note that the disclosed feature augmentation technique is not limited to time-frequency grid representations or the audio recordings.

Now, consider the same patient speaking in a noisy and reverberant environment which describes the desired semantic in a noisy and reverberation effects. The goal is to create an alternative feature from the cough sound feature that represents the patient coughing in a noisy and reverberant environment using the patient's speech sound in the noisy and reverberant environment.

To do this, a pre-trained network, such as the VGG-ish Model trained on audio events (https://github.com/tensorflow/models/tree/master/research/audioset) or the network explained in FIG. 14 earlier, is used to extract content and semantics from the features, in this case, the features are audio features.

We now define two cost functions that are used to train a convolutional neural network that generates the desired feature. The first one is a content cost function as shown in Equation 8:

$$J_{Content}(Content,Generated)=(4*n_H*n_W*n_C)^{-1}*\Sigma_{all} (\alpha^C-\alpha^G) \quad [8]$$

wherein $n_H$, $n_W$, $n_C$ represent the dimensions of a predetermined hidden layer from the pre-trained network, $\alpha^C$ represents the output in response to activation from one of the middle layers when the content image has forward propagated through the pre-trained network and $\alpha^G$ represents the output from the same activation layer from the forward propagated generated spectrogram (e.g., this can be a white noise spectrogram of size 64 by 500 or perhaps a better initialization based on the desired generated sound).

The second cost function is a semantic cost function described in Equation 9:

$$J_{semantic}(\text{Semantic,Generated}) = (4*n_H^2*n_W^2*n_C^2)^{-1}*\Sigma_i^{nC}\Sigma_j^{nC}(Ge_{ij}^S - Gr_{ij}^G)^2, \quad [9]$$

wherein Gr is a gram matrix that is calculated by taking the dot product of the reshaped activation function with its transpose wherein the size of the first matrix is $n_C$ by $n_H*n_W$ and the second matrix is $n_H*n_W$ by $n_C$. The gram matrix measures the correlation of filters from the output of the activation function on a specific layer (or weighted average of multiple layers) that, in this example, would represent the semantic of the audio feature. It is important to note that the choice of the example audio that represents the semantic is important in creating a realistic feature. The gram matrices for the semantic and generated audio features are calculated by forward propagating them through the pre-trained network. The final cost function is a weighted sum of the content and semantic cost functions as shown in Equation 10:

$$J_G(\text{Generated}) = \alpha * J_{Content}(C,G) + \beta * J_{semantic}(S,G). \quad [10]$$

Once the content and semantic features are forward propagated through the network and the cost function is determined, the initial generated feature (i.e., random noise) is propagated through the network given $J_{Content}$, $J_{Semantic}$, and $J_G$ as cost functions wherein the generated feature is updated at every step until convergence criterion is met by selecting the input feature to the pre-trained model as the output feature.

Figure 24:
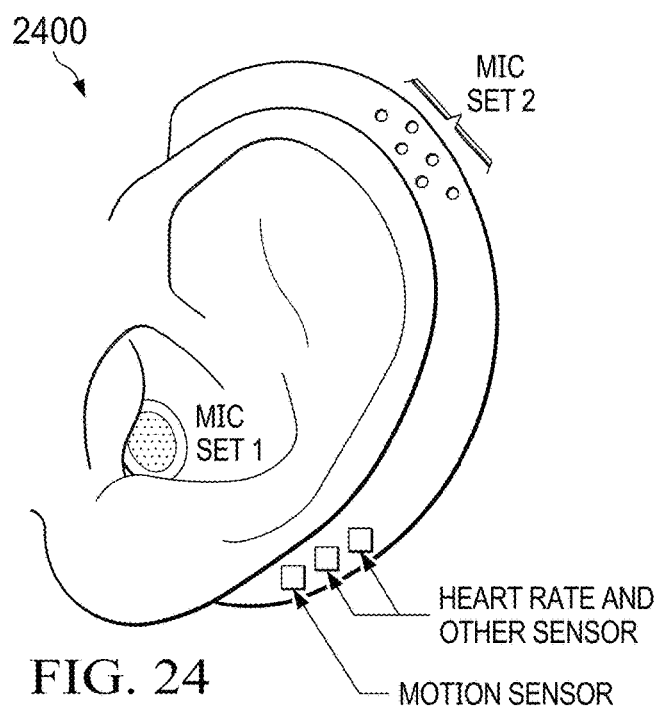
FIG. 24 illustrates a hearing device that goes inside the user's ear canal or around the user's ear and contains microphones close to the inner canal and outside the ear and one or more motion sensors, according to an embodiment.

Referring to FIG. 24, a device (2400) is shown that goes inside the user's ear canal (e.g., earbuds) or around the user's ear (e.g., headset) and contains microphones close to the inner canal and outside the ear, a motion sensor, among other sensors to track heart rate, oxygen level, etc. These sensors work together to monitor the patient's symptoms when the patient does not have access to a far field monitoring device. Using two microphone arrays, one inside the ear and one outside the ear, allows sounds to be detected that are barely audible to naked ears, such as wheezing captured by the inner microphone, teeth grinding, and sleep disorder symptoms such as snoring. Another purpose of the device is to detect the respiratory rate of the user which can help detect symptoms such as breathlessness. An additional advantage of using multiple microphones is that the outer microphone can be used to record ambient sounds which can be used to denoise the audio signals to assure that a clean audio signal is recorded.

This device 2400 is advantageous compared to other wearables as the noise induced by clothing or movements is minimal. The data collected from the microphone and other sensors can be fused and trained to predict different symptoms. The fusion of microphones and motion sensors can help in reducing false alarms. For example, if the motion sensor does not detect movement of the user when the user coughs, the cough may be rejected as background noise since no motion was detected. Any of the schemes discussed earlier can be applied here as well, such as the schemes described in reference to FIGS. 4 and 5.

Figure 25:
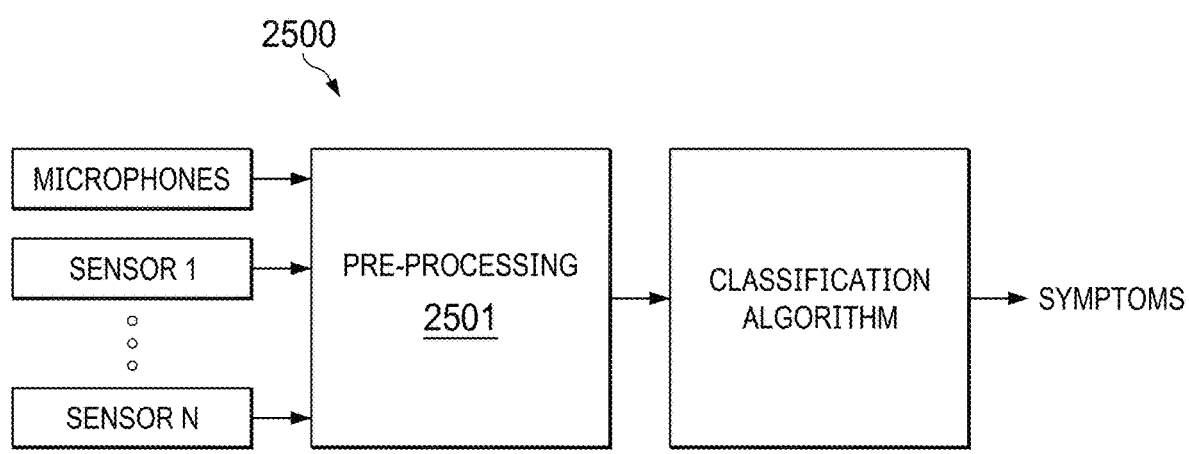
FIG. 25 illustrates the preprocessing of audio data and motion data to assure the data is clean and that the audio/motion data are input to a classification algorithm at the same rate, according to an embodiment.

In an embodiment, the preprocessing (2501) of the sensory signals might be done on each individual sensor as shown in FIG. 25. Once the features are preprocessed, they are fed to a classification algorithm (401) (FIG. 4) to predict the symptoms with higher precision and recall. In an embodiment, the classification algorithm might use an additional regularization on the input feature layer to account for missing values at different timestamps.

In an embodiment, sensors can be synchronized using an activation signal. For example, a microphone samples pressure in 44.1 kHz rate and a gyroscope sensor output data rate could be 2000 Hz. The sensors can be synchronized by adding redundant data for the sensor with less resolution or downsample the sensor data to the lowest data rate of the sensors. Because different sensors capture different types of data, an activation signal, such as sending a shockwave to the device and synchronize all sensors by undoing the time delay from the received signal.

Figure 26:
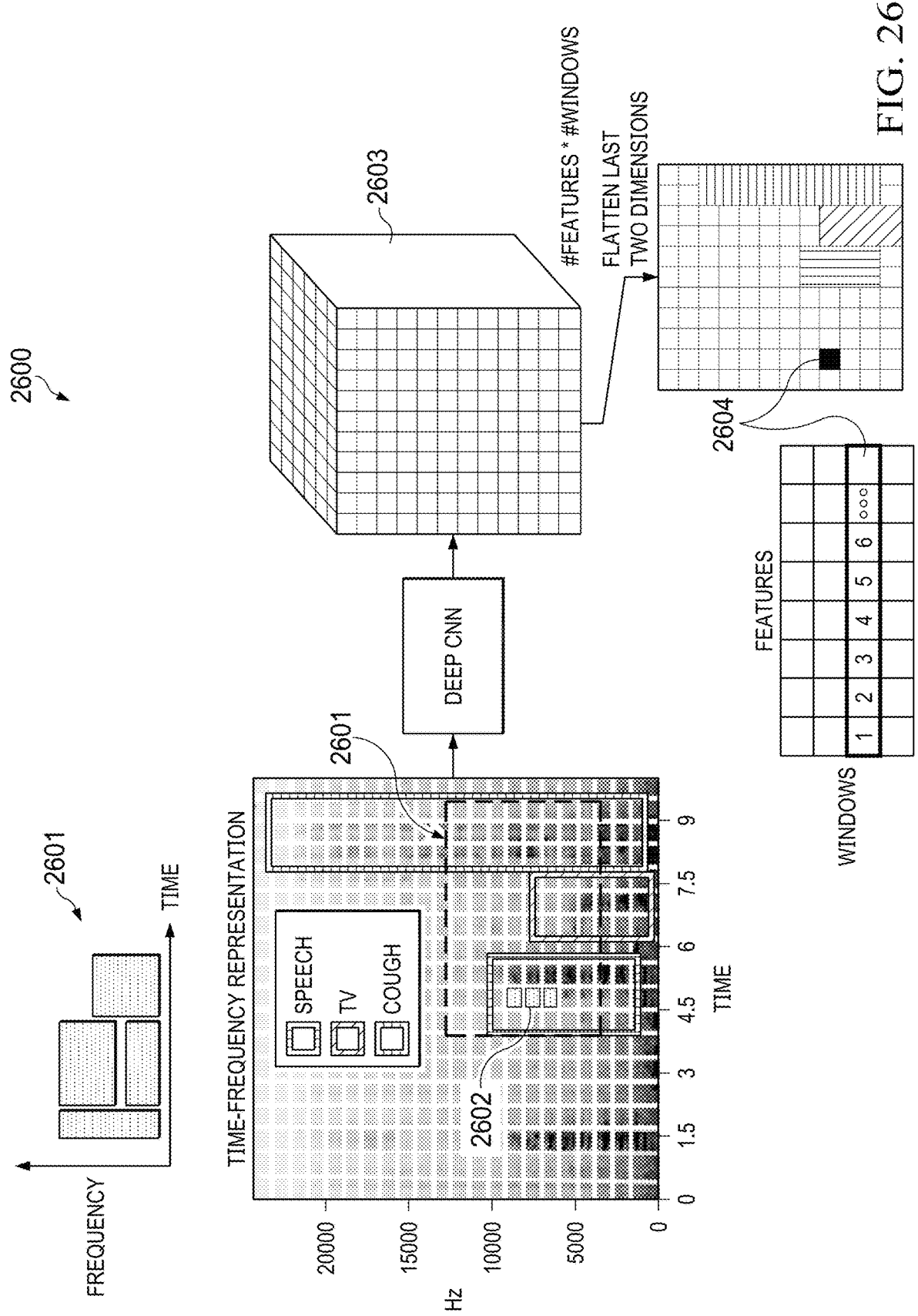
FIG. 26 illustrates a convolutional neural network (CNN) for localizing and classifying overlapping audio events.

In another embodiment, audible symptoms are detected along with other sound events that may be occurring within the same analysis window. i.e., overlapping in time. Referring to FIG. 26, a time-frequency representation of an audio signal such as a spectrogram is shown. It is possible to detect multiple sound events within the same analysis window such as speech, television sound, cough, kitchen noise, etc. Due to the resolution of the analysis window, a classifier may not be able to detect all three events and thus likely misclassify the audio segment being analyzed.

To address this issue, a predetermined variations of time-frequency windows can be defined that are optimized to detect a certain sound events (2601). Data is annotated in the time-frequency domain (2602) by assigning the time-frequency bins (e.g., comparing the boundaries of the current analysis window) for a certain sound to the closest grid box. Once data is annotated, a convolutional neural network can be trained to map the spectrogram to a lower resolution spectrogram, wherein each element in the target corresponds to one grid box in the input sound (2603). Careful consideration should be made in designing the CNN architecture to achieve this correspondence between the input and target. In an embodiment, the target tensor is a four-dimensional array (with dimensions as frequency, time, number of features and number of windows). For easier visualization, the last two dimensions can be flattened out so that each element of the target matrix is a matrix itself (2604). This matrix contains features for each predetermined window and grid box. This feature vector can contain information such as whether there is an audio event in this grid box, and if there is, which class does it belong to. The class label will then belong to the maximum class confidence value over all windows and classes for a specific grid box. One can further prune overlapping windows using techniques such as non-maximum suppression. Once the network is trained it can be used to predict the labels for several classes for each grid box even if sound events partially overlap in time or frequency dimensions.

In an embodiment, a user's future disease state over a span of several days can be determined based on several features such as current and past symptoms, current and past weather conditions and future predictions of user's health condition, user's past and current compliance, etc. The user can be advised to take certain actions based on future diseases state to prevent a potential illness. For example, two sets of predictions can be made wherein the probability of the disease state is determined for example if the user would continue not complying with the suggested actions and another if the user would comply. As such a user can take suggested actions based on the future predictions. Such predictions could help the user identify triggers and encourage compliance through forming good habits.

Figure 27:
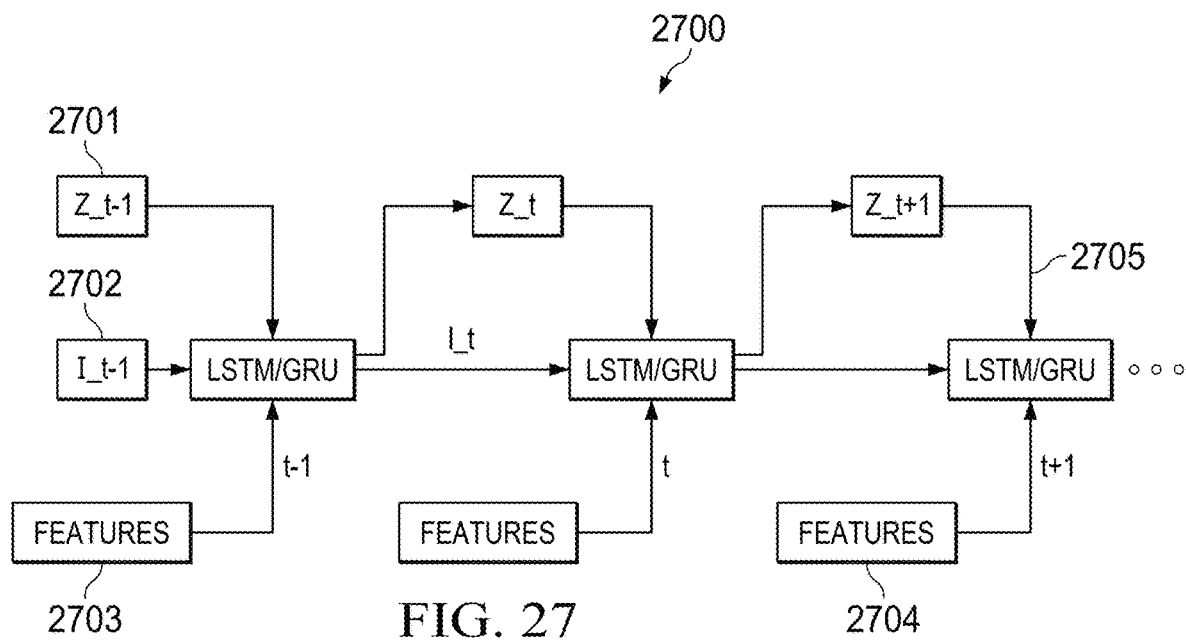
FIG. 27 illustrates a recurrent neural network for determining future predictions of a user's disease state based on past and current data as well the predictions for future data, according to an embodiment.

Referring to FIG. 27, a recurrent network is shown that can model future predictions of a user's disease state. For simplicity a one layer LSTM cell is used, however as can be appreciated by those with ordinary skill in the art, this network can be made deeper by adding feedforward network and softmax layers at the output of the LSTM cells, multiple LSTM layers may also be added in parallel, GRU cell can replace LSTM cells, etc. LSTM or GRU cells can learn to keep or forget information from the past to determine the disease state of the user with more certainty using the information collected from the past and current, as well as network predictions. The feature vector (2703) could contain information such as symptoms, weather conditions, compliance, etc. The internal state (2702) and the previous output can be initialized by random values at the beginning of time. The prediction vector containing the disease state and other useful predictions from each time stamp is fed to the next cell along with the current feature vector (2701). If some of the feature vector elements do not exist, such as user's symptoms in the future, they can be replaced by the user's current features or left blank (2705). In many cases, the future time stamp would contain soft likelihoods of potential triggers, and predicted disease state based on the user's compliance, past and current disease state, etc. to better account for what the user will actually experience in the future to help prevent, prepare, or educate the user for likely upcoming scenarios.

In an embodiment, a summary of each patient is created and put into a profile as they are monitored over a certain period of time. This profile can contain but is not limited to information, such as the user's age, disease progress, compliance with the service, taking medication on time, user's zip code, triggers, treatment plan, respiratory health, etc. Patients are then clustered into a few predetermined categories based on one or more of this information to enhance the user's experience and keep them engaged at all times. For example, users that have high compliance and are under the same treatment plan might get clustered into one group. These users are then assigned to a human coach and may be provided with similar practices and guidelines. For example, patients with similar respiratory symptoms (or experiencing a similar level of stress because of their condition) and treatment compliance assigned to the same category may receive the same recommendation for medications or the patients categorized in the same location may receive the same recommendation to avoid a trigger. This can help the human coach to monitor more patients at the same time as patients in that group could have similar interests, characteristics, or symptoms. Such clustering can be done in an unsupervised or supervised manner and can result in new insights that might not have been possible to find without having access to user's profiles over time. The data of users who get clustered into a specific group can be used to train a model that is more personalized to that group by adapting the detection model on that set of data using techniques, such as transfer learning or manually adjusting the model's parameters. This will assure a higher specificity and sensitivity when detecting symptoms.

Figure 28:
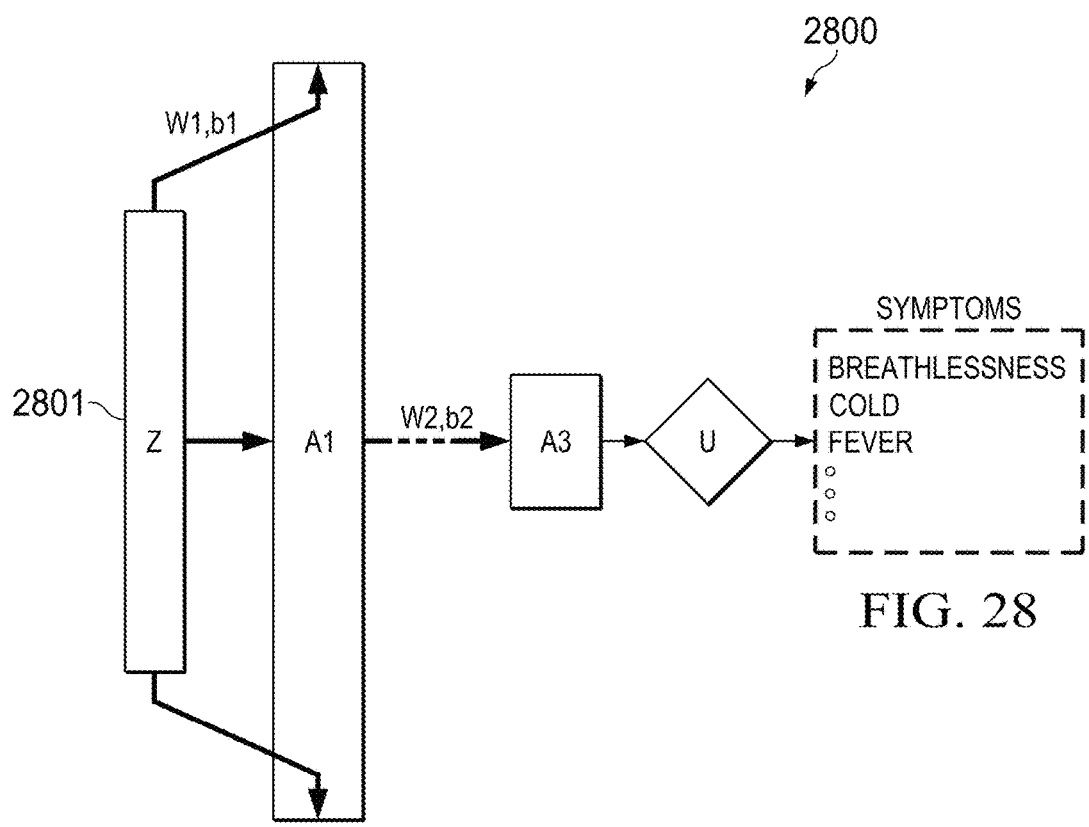
FIG. 28 illustrates a neural network for predicting symptoms from a patient's speech recording, according to an embodiment.

In an embodiment, a patient's speech is analyzed to detect a disease related symptom(s). Consider the following example: a patient is prompted to read a sentence while an electronic device is recording the patient. Such a sentence could for example contain several vowels and consonants wherein a patient who is experiencing breathlessness might have trouble reading. For example, consider the sentence, "She had your frosty white suit in greasy hot wash water all afternoon," with several vowels and consonants one after another. To train an AI algorithm to detect a symptom from the recorded sentence the patient is requested to record a given sentence on a periodic basis while in the background a patient's symptoms are tagged through sensory data. A neural network is then trained with patient's speech recordings as the input and the corresponding symptoms as the output as shown in FIG. 28. Such network can also be used in conjunction with sensory data as a prior information to make more accurate decisions about patient's symptoms, disease state, etc.

Figure 29:
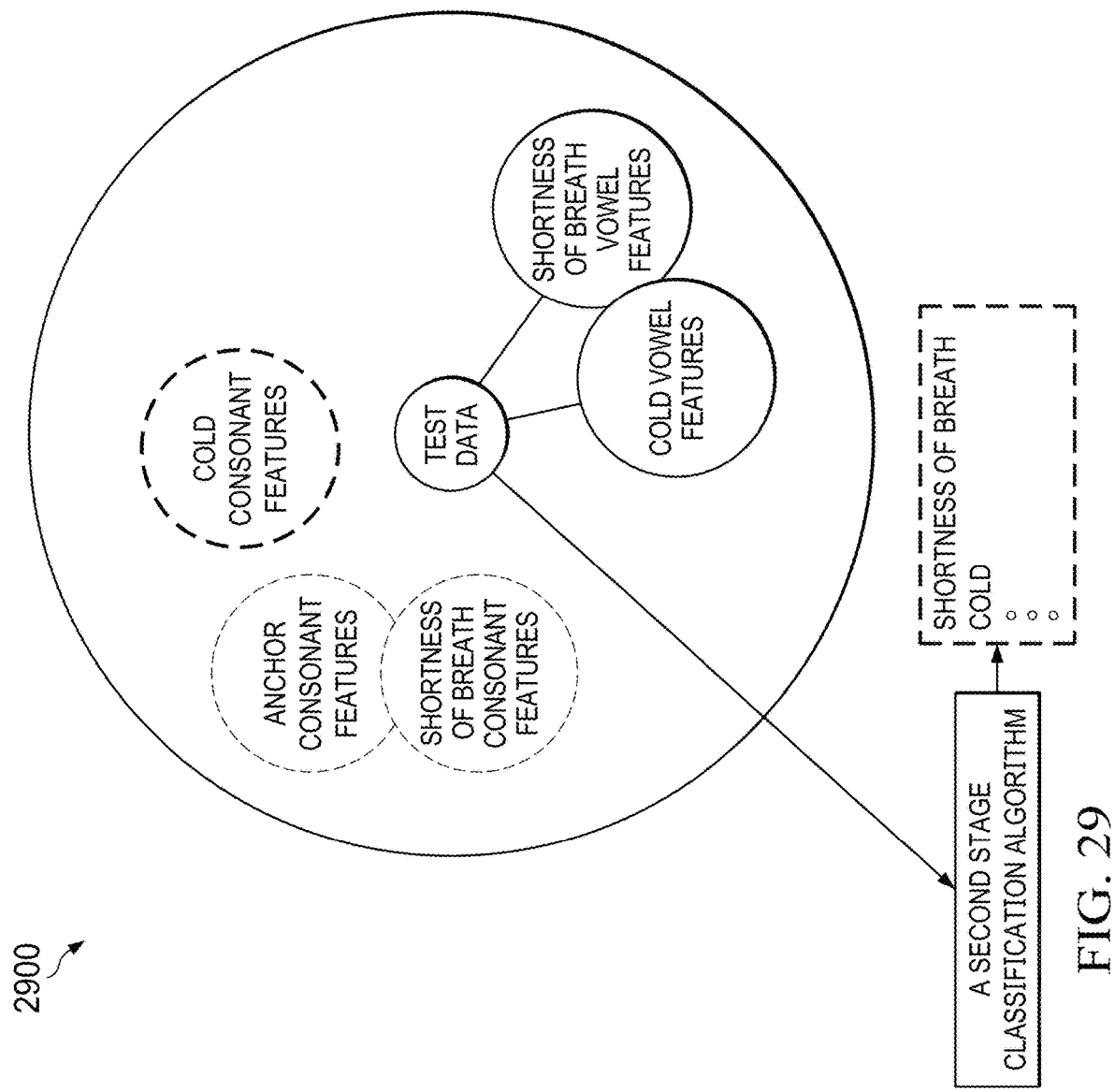
FIG. 29 illustrates an unsupervised technique for designing sentences that are optimized for detecting a predetermined set of symptoms, according to an embodiment.

In another embodiment, a method is described to design speech stimuli that would detect and emphasize an existing symptom in a patient. There are two groups of data: patient's speech where no symptoms were detected, i.e., anchor signals and any other speech recordings that corresponded to a particular symptom(s), i.e., symptom signal. For example, it might be a case for a patient that vowels are harder to pronounce when the patient is short of breath. Therefore, if a patient is prompted to read a sentence that contains many vowels, then the anchor signal and the symptom signal would have very different pronunciation of the vowels. Therefore, it can be inferred that a sentence with more vowels could directly reveal this existing symptoms. A new sentence can also be designed to detect other disease-related symptoms of the user that wasn't discovered by the first sentence, i.e., the second sentence is designed based on the neural network prediction on the first sentence. To design such sentences an unsupervised technique can be used to cluster features extracted from the anchor and the symptom signals, wherein, features could represent vowels, consonants, or the transition from a vowel to a consonant, etc. The features that get clustered closer to the anchor signal centroid can be interpreted as not important for conveying the symptom. A simple example is illustrated in FIG. 29 to demonstrate how such decisions can be inferred. This is not to limit the scope of this embodiment as it can be appreciated by a skilled in the art a soft clustering in higher dimensions with a more sophisticated measure of similarity would provide a more robust prediction. A downside of clustering can be that a patient might have a similar difficulty with different symptoms. As such a second stage classification can be used to further prune patient's pronunciation of a sentence into different symptom labels.

Figure 30:
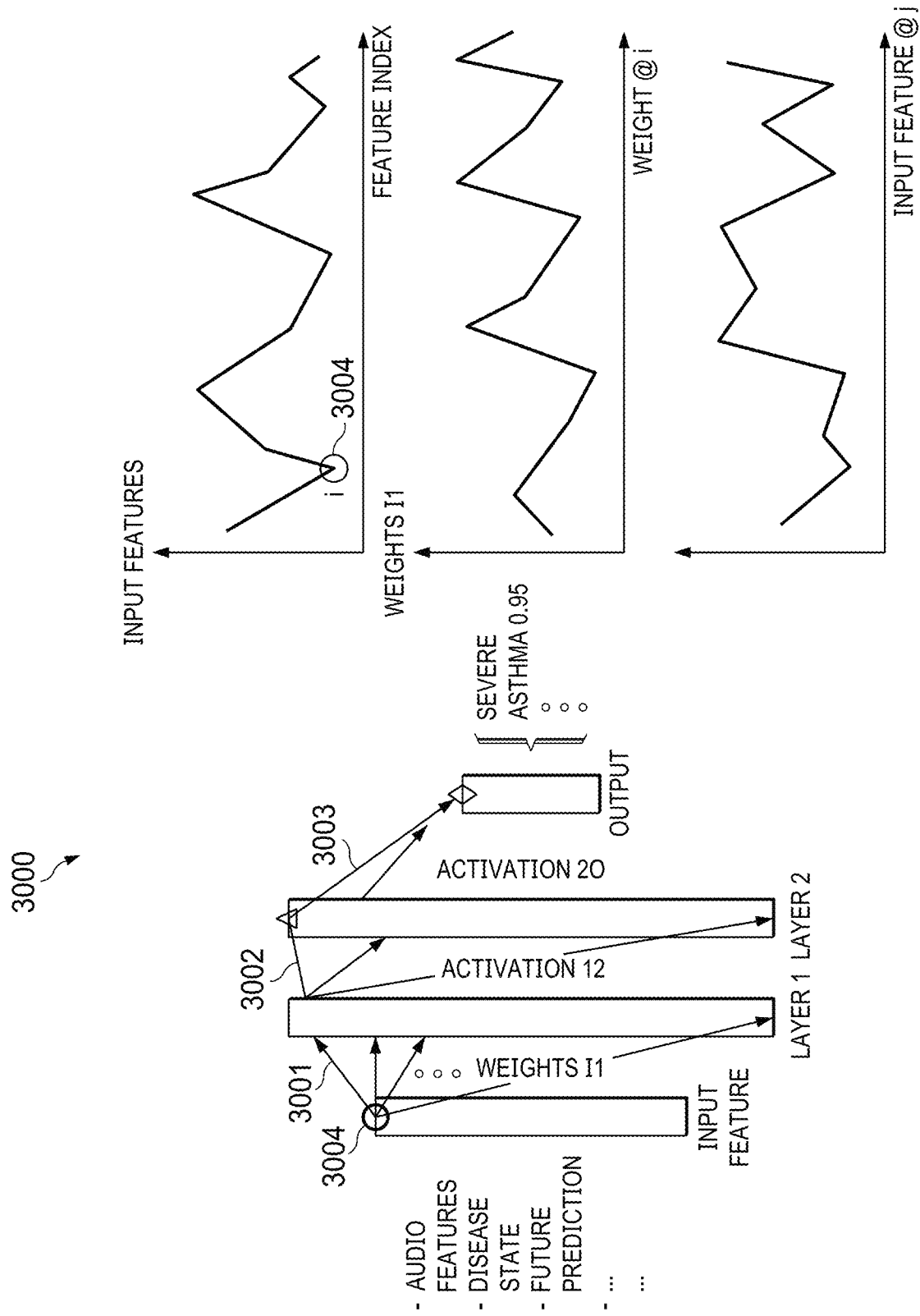
FIG. 30 depicts a method for interpreting a neural network prediction, according to an embodiment.

In another embodiment, a method is described to interpret why the AI algorithms have made a certain decision or symptom prediction to help physician and the patient understand the result and further gain user's trust. To further motivate this method consider this example wherein the algorithm has determined that severe asthma is likely as the inference of one of the discussed neural networks indicate. To interpret why an algorithm made such predictions one approach is to analyze and track the weighted average of the activation functions from different input features from selected layers. Consider FIG. 30 wherein the feature, weights, and activation values for selected layers are visualized for a given input feature. To understand how much a feature value affects the final prediction, the weights from the input feature is traced to the final prediction. One of the reasons deep neural networks are harder to explain and are known to be a "black box" is because the weights from one neuron connects to every other neuron in the next layer and a simple look at the histogram's weights might not be sufficient to explain why a certain output target was more likely than others. As depicted in 3001 the weights originating from one of the input features can be easily tracked to any neurons in the second layer. Assume that the first layer is the input feature vector denoted as $X_1=[x_{10}, x_{11}, \ldots ]$, the second layer was the final output layer and the fifth element in the second layer is the most likely prediction, $n_{25}$. The weights from the first neuron in the input feature vector as $W_{12}=[w_{121}, w_{122}, w_{123}, \ldots ]$ wherein the most significant digit denotes the neuron index at the second layer. For simplicity, the non-linear activation functions can be ignored. The goal here is to find the $x_{1j}$s that impacted the decision $n_{25}$ the most and therefore explains why the network predicted severe asthma, e.g., if the audio features have a higher impact than the network predicted because of overnight audible recordings. Note that the same procedure can also be used to explain why the network predicted that an outcome is unlikely.

In the two layer network discussed above simply sorting the values of W12*X1 over each input feature would identify the feature vectors that affected each output label the most. This process can be extended to more layers by keeping track of the input feature elements impact on each layer. To find the most impactful input feature vector, the weights connected to the output label are backtracked. For example, once the most impactful neuron at the layer next to the final layer is determined, then the same process can be done to find the neuron that was most impactful for the layer before it. This process is repeated until the input feature(s) that impacted the network decision are determined through recursion as shown in Equation 11 wherein $f_{L-1,j}$ corresponds the most impactful element in layer L-1 for neuron k at layer L.

$$f_{L-1,j} = \mathrm{argmax}_k (W_{i,(L-1,L)} X). \quad [11]$$

Once the most impact score neuron(s) are determined there are multiple ways to interpret and communicate the interpretations to a user. Impact score can be calculated for each input neuron by sorting all input features based on their impact value on a predetermined prediction and assign a soft value denoted as their impact score to each neuron that describes their contribution to that prediction.

Figure 31:
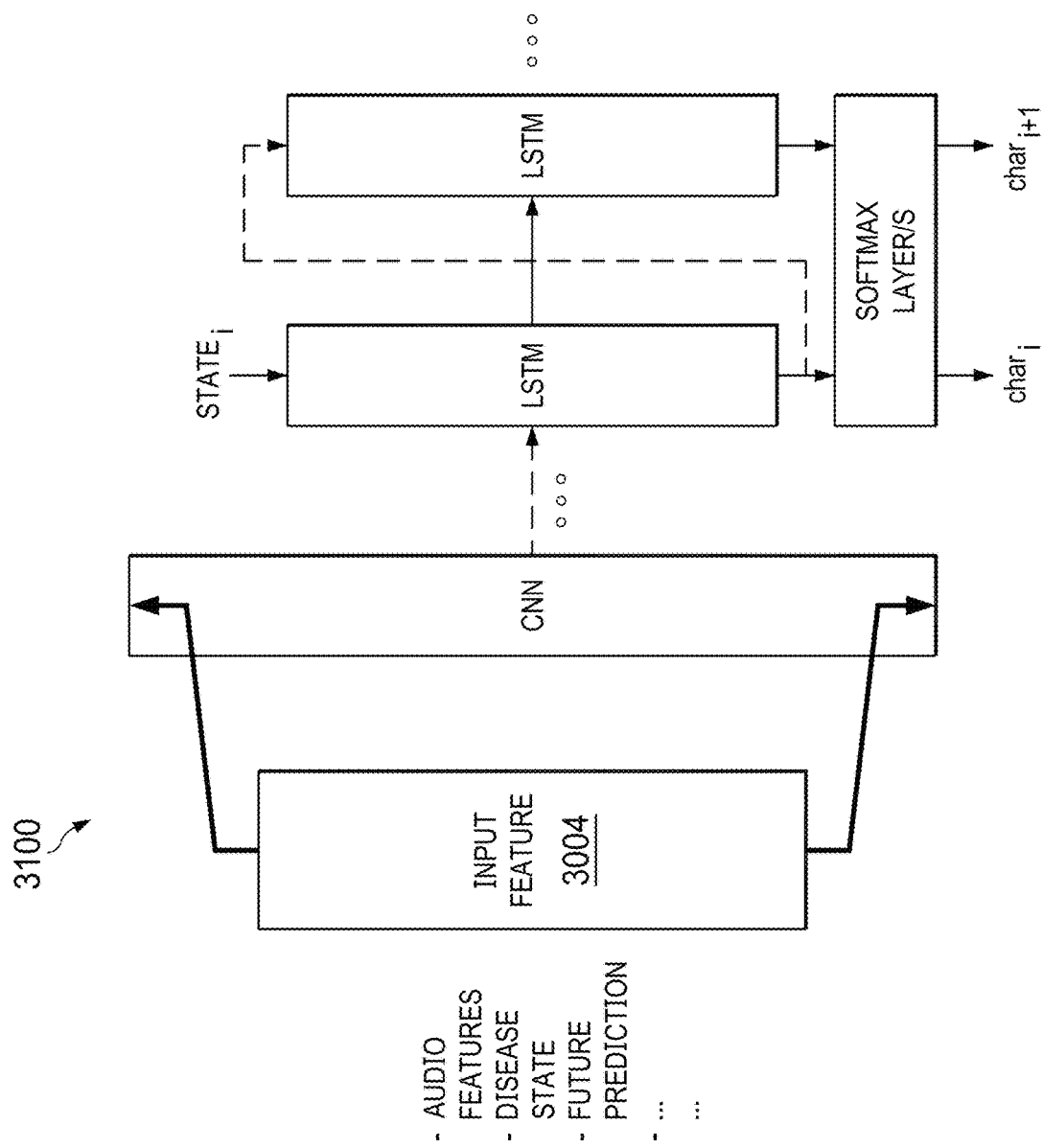
FIG. 31 depicts a method for generating a sentence that describes the interpretation of a neural network prediction, according to an embodiment.

In an embodiment, a table of interpretations is prepared for different scenarios, so that the most likely scenarios can be looked-up in the table based on the predicted most impactful neuron(s). Another approach is to create a dataset describing decisions made by the network with a sentence, e.g., "Network has classified the patient in severe category because it will be raining tomorrow and that will exacerbate the user's symptoms." This sentence is provided by an annotator who is manually interpreting the AI decision based on the feature impact score. This dataset now contains the ranking of the input feature based on their impact score described earlier as input to the network and the sentences as the label. A network similar to those networks shown in FIGS. 20 and 27 can then be trained on this dataset that interprets the network's prediction by generating a sentence as shown in FIG. 31.

Example embodiments disclosed include techniques for determining the symptoms, disease or a disease state of a patient based on observed (i.e., captured through multimodal sensors) and reported data obtained continuously in real-time or when prompted, such as uncontrolled asthma, sleep disorders, respiratory conditions, and other diseases.

Example embodiments disclosed herein can be employed to track and detect symptoms that can include but are not limited to coughs, wheezing, snoring, teeth grinding, etc., wherein data is collected from sensors and non-sensory data, such as an air quality index for the location where the patient resides, weather conditions, patient body temperature, the user's manual data entry, transcription from a discussion with a coach, etc., and predicted data in the future and available information from the past. Sensory data is monitored continuously using devices such as microphones found in handheld devices, smart speakers, or when prompted using a digital stethoscope, peak flow meter, and/or thermometer.

Example embodiments described herein include a method wherein a microphone or a set of microphones are used to gather relevant auditory information from a user which is then feed to classification algorithms to determine a user's health, sleeping quality, etc.

Example embodiments disclosed herein include techniques for detecting a disease or monitoring a disease state based on multimodal sensory and non-sensory data, wherein the trend of the disease state overtime can determine the effectiveness of the medications.

Example embodiments disclosed herein include methods wherein room acoustics, devices post-processing, and other variabilities of a specific audio signal, such as equalization, noise, etc., are modelled through signal processing and machine learning techniques to create more realistic synthesized recordings of an auditory event as well as techniques for augmenting sensory features using convolutional neural networks.

Example embodiments disclosed herein include a method wherein a sound captured by one or more microphones is classified as a symptom in real-time.

Example embodiments disclosed herein include a method wherein a second classification algorithm is cascaded to a first classification algorithm to detect true positives from false positives. The goal of the additional classifiers is to reduce false positives and improve the classification precision and accuracy, as well as personalizing the model for specific conditions.

Example embodiments disclosed herein include a method wherein an event classifier model is adapted periodically based on the data collected from users over time. Such adaptation helps in suppressing false alarms as well as personalizing a model that learns a user's habits and environment through model adaptation and suggest better actions to prevent illnesses in the future.

Example embodiments disclosed herein include a method wherein a dynamic audio summary (e.g., an audio bite) is created and presented to a physician to help identify possible causes of the symptom, disease, disease state, etc.

Example embodiments disclosed herein include a method for discovering potential triggers that may cause a change in the user's symptoms, disease, or disease state.

Example embodiments disclosed herein include a method wherein content and semantic audio data are used to generate a new audio feature that represents the content audio data generated with the semantic audio data style.

Example embodiments disclosed herein include a method wherein several profiles are generated for patients, wherein each patient profile describes a category of patients with similar recommended action plans.

Example embodiments disclosed herein include a method wherein a desired, an anchor, and a negative audio event generate a feature for the desired audio event.

Example embodiments disclosed herein include a device that is inserted or worn around the ear. The device contains microphones outside and inside the ear canal as well sensors to monitor motion, pulse oxygen sensor, and heart rate sensor that measure's user vitals and motions during an abnormal event, such as a respiratory event, falling, moaning in pain, etc.

Example embodiments disclosed herein include a method determining boundaries of an audio event in a time-frequency representation by training a convolutional neural network on several audio data with a set of analysis windows.

Example embodiments disclosed herein include a method for recommending actions to users to prevent symptoms or disease severity by predicting user's future states using LSTM/GRU networks.

Example embodiments disclosed herein include designing a sentence to effectively predict a user's symptoms using only the user's speech utterance.

Example embodiments disclosed herein include a method for interpreting AI algorithm decision making and conversing the results in words.

Specifically, in accordance with any of the example embodiments, the processes described above regarding FIGS. 1-27 may be implemented as a computer program product including a computer program tangibly embodied on a machine-readable medium and the computer program including program code for performing the method 801. Generally, various example embodiments disclosed herein may be implemented in hardware or special purpose circuits, software, logic or any combination thereof. Some aspects may be implemented in hardware, while other aspects may be implemented in firmware or software which may be executed by a controller, microprocessor or other computing device.

While various aspects of the example embodiments of the present invention are illustrated and described as block diagrams, flowcharts, or using some other pictorial representation, it will be appreciated that the blocks, apparatus, systems, techniques or methods described herein may be implemented in, as non-limiting examples, hardware, software, firmware, special purpose circuits or logic, general purpose hardware or controller, or other computing devices, or some combination thereof.

Additionally, various blocks shown in the flowcharts may be viewed as method steps, and/or as operations that result from operation of computer program code, and/or as a plurality of coupled logic circuit elements constructed to carry out the associated function(s). For example, embodiments disclosed herein include a computer program product comprising a computer program tangibly embodied on a machine readable medium, in which the computer program containing program codes configured to carry out the methods as described above.

In the context of the disclosure, a machine readable medium may be any tangible medium that may contain, or store, a program for use by or in connection with an instruction execution system, apparatus, or device. The machine readable medium may be a machine readable storage medium. A machine readable medium may include but is not limited to an electronic, magnetic, optical, electromagnetic, infrared, or semiconductor system, apparatus, or device, or any suitable combination of the foregoing. More specific examples of the machine readable storage medium would include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

Computer program code for carrying out the disclosed embodiments may be written in any combination of one or more programming languages. These computer program codes may be provided to a processor of a general purpose computer, special purpose computer, or other programmable data processing apparatus, such that the program code, when executed by the processor of the computer or other programmable data processing apparatus, cause the functions/operations specified in the flowcharts and/or block diagrams to be implemented. The program code may execute entirely on a computer, partly on the computer, as a stand-alone software package, partly on the computer and partly on a remote computer or entirely on the remote computer or server.

Further, while operations are depicted in a particular order, this should not be understood as requiring that such operations be performed in the particular order shown or in sequential order, or that all illustrated operations be performed, to achieve desirable results. In certain circumstances, multitasking and parallel processing may be advantageous. Likewise, while several specific implementation details are contained in the above discussions, these should not be construed as limitations on the scope of any invention, or of what may be claimed, but rather as descriptions of features that may be specific to particular embodiments of particular inventions. Certain features that are described in this specification in the context of separate embodiments may also may be implemented in combination in a single embodiment. Conversely, various features that are described in the context of a single embodiment may also may be implemented in multiple embodiments separately or in any suitable sub-combination.

Various modifications, adaptations to the foregoing example embodiments disclosed herein may become apparent to those skilled in the relevant art in view of the foregoing description, when read in conjunction with the accompanying drawings. Any and all modifications will still fall within the scope of the non-limiting and example embodiments of this invention. Furthermore, other embodiments not disclosed herein will come to mind to one skilled in the art as having the benefit of the teachings presented in the foregoing descriptions and the drawings.

The invention claimed is:

1. A method comprising:
   obtaining, using one or more processors of a device, a first speech recording of a pre-determined first sentence uttered by a user, the pre-determined first sentence designed to detect a pre-defined set of disease-related symptoms exhibited by the user;
   predicting, using a neural network with the first speech recording as input a first set of one or more disease-related symptoms of the user, the neural network trained on features extracted from user utterances as input and corresponding symptoms as output; and
   designing, using an unsupervised learning technique, a second sentence, the second sentence designed to emphasize one or more features of the first pre-determined sentence;
   obtaining a second speech recording of the second sentence uttered by the user; and
   processing the second speech recording through the neural network to predict symptoms using the second sentence.

2. The method of claim 1, wherein the pre-determined first sentence contains one or more vowels and consonants to enable the detection of the pre-defined set of disease-related symptoms.

3. The method of claim 1, wherein the neural network is trained on features extracted from utterances collected from a set of users exhibiting one or more of the disease-related symptoms in the pre-defined set of disease-related symptoms.

4. A system comprising:
   one or more processors;
   memory storing instructions that when executed by the one or more processors, cause the one or more processors to perform operations comprising:

obtaining a first speech recording of a pre-determined first sentence uttered by a user, the pre-determined first sentence designed to detect a pre-defined set of disease-related symptoms exhibited by the user;

predicting, using a neural network with the first speech recording as input a first set of one or more disease-related symptoms of the user, the neural network trained on features extracted from user utterances as input and corresponding symptoms as output; and designing, using an unsupervised learning technique, a second sentence, the second sentence designed to emphasize one or more features of the pre-determined first sentence;

obtaining a second speech recording of the second sentence uttered by the user; and processing the second speech recording through the neural network to predict symptoms using the second sentence.

5. The system of claim 4, wherein the pre-determined first sentence contains one or more vowels and consonants to enable the detection of the pre-defined set of disease-related symptoms.

6. The system of claim 4, wherein the neural network is trained on features extracted from utterances collected from a set of users exhibiting one or more of the disease-related symptoms in the pre-defined set of disease-related symptoms.

7. The method of claim 1, wherein the neural network is trained on two groups of data, a first group of data corresponding to the user uttering an anchor sentence where no symptoms are detected and a second group of data corresponding to the user uttering a same sentence when there is a symptom detected.

8. The method of claim 2, wherein the second sentence is generated based on the predictions output by the neural network or predictions using the pre-determined first sentence to detect further symptoms exhibited by the user or further confirm existing symptoms exhibited by the user.

9. The method of claim 1, wherein the unsupervised learning technique is clustering, and the second sentence is designed by generating a second sentence cluster including one or more features of the second sentence and measuring a distance of the second sentence cluster from a previously generated first sentence cluster.

10. The method of claim 9, wherein the one or more features of the second sentence represent at least one of vowels, consonants, or the transition from a vowel to a consonant.

11. The method of claim 9, wherein if the distance between the first sentence cluster and an anchor sentence cluster is less than a pre-determined threshold the first sentence is interpreted as not conveying a symptom.

12. The method of claim 11, wherein if the distance between the first sentence cluster and the anchor sentence cluster is larger than the pre-determined threshold then one or more segments of the pre-determined first sentence are emphasized in generating the second sentence.

13. The method of claim 9, wherein the distance measured is one of a Euclidean distance, Kullback-Leibler divergence or an inverse similarity measure.

14. The system of claim 4, wherein the unsupervised learning technique is clustering and a second stage classifier is attached to a clustering model to further detect symptoms from the utterance of the second sentence by the user.

15. The system of claim 5, wherein the neural network is trained on two groups of data, a first group of data corresponding to the user uttering an anchor sentence where no symptoms are detected and a second group of data corresponding to the user uttering a same sentence when there is a symptom detected.

16. The system of claim 14, wherein the second sentence is generated based on the predictions output by the neural network or predictions using the pre-determined first sentence to detect further symptoms exhibited by the user or further confirm existing symptoms exhibited by the user.

17. The system of claim 15, wherein the second sentence is designed by clustering one or more features of the anchor sentence into an anchor sentence cluster and clustering one or more features of the first sentence and measuring a distance across the features in the anchor sentence cluster and the first sentence cluster.

18. The system of claim 17, wherein the one or more features represent at least one of vowels, consonants, or the transition from a vowel to a consonant.

19. The system of claim 18, wherein if the distance between the first sentence cluster and an anchor sentence cluster is less than a pre-determined threshold the first sentence is interpreted as not conveying a symptom.

20. The system of claim 19, wherein if the distance between the first sentence cluster and the anchor sentence cluster is larger than the pre-determined threshold then one or more segments of the pre-determined first sentence are emphasized in generating the second sentence.

21. The system of claim 17, wherein the distance measured is one of a Euclidean distance, Kullback-Leibler divergence or an inverse similarity measure.

22. The system of claim 17, wherein the unsupervised learning technique is clustering and a second stage classifier is attached to a clustering model to further detect symptoms from the utterance of the second sentence by the user.

* * * * *